US012676243B2

(12) United States Patent
Johnston et al.

(10) Patent No.: US 12,676,243 B2
(45) Date of Patent: Jul. 7, 2026

(54) QUANTIFYING VARIATION IN SURGICAL APPROACHES

(71) Applicant: DIGITAL SURGERY LIMITED, London (GB)

(72) Inventors: Helena Elizabeth Anne Johnston, London (GB); Carole RJ Addis, London (GB)

(73) Assignee: DIGITAL SURGERY LIMITED, London (GB)

( * ) Notice: Subject to any disclaimer, the term of this patent is extended or adjusted under 35 U.S.C. 154(b) by 281 days.

(21) Appl. No.: 18/282,317

(22) PCT Filed: Apr. 14, 2022

(86) PCT No.: PCT/EP2022/060032
§ 371 (c)(1),
(2) Date: Sep. 15, 2023

(87) PCT Pub. No.: WO2022/219127
PCT Pub. Date: Oct. 20, 2022

(65) Prior Publication Data
US 2024/0161934 A1 May 16, 2024

Related U.S. Application Data

(60) Provisional application No. 63/297,283, filed on Jan. 7, 2022, provisional application No. 63/208,171, filed
(Continued)

(51) Int. Cl.
| *G06V 20/40* | (2022.01) |
| *G16H 30/40* | (2018.01) |
| *G16H 70/20* | (2018.01) |

(52) U.S. Cl.
CPC ............. *G16H 70/20* (2018.01); *G06V 20/41* (2022.01); *G06V 20/49* (2022.01); *G16H 30/40* (2018.01)

(58) Field of Classification Search
CPC ........ G16H 70/20; G16H 30/40; G06V 20/41; G06V 20/49; G06V 20/70
See application file for complete search history.

(56) References Cited

U.S. PATENT DOCUMENTS

| 10,147,052 B1 | 12/2018 | Lendvay et al. |
| 10,607,158 B2 | 3/2020 | Lendvay et al. |
| | (Continued) | |

OTHER PUBLICATIONS

Germain Forestier, Francois Petitjean, Laurent Riffaud, Pierre Jannin. "Non-Linear Temporal Scaling of Surgical Processes". Artificial Intelligence in Medicine, Elsevier. < http: / /www.sciencedirect. com/ science/article/pii/S0933365714001225>. (Year: 2014).*
(Continued)

*Primary Examiner* — Amandeep Saini
*Assistant Examiner* — Jaspreet Kaur
(74) *Attorney, Agent, or Firm* — CANTOR COLBURN LLP; Robert Crist

(57) ABSTRACT

An aspect includes a computer-implemented method that quantifies variations in surgical approaches to medical procedures. Surgical videos documenting multiple cases of a medical procedure are analyzed to identify variations in surgical approaches used by service providers when performing the medical procedure. According to some aspects, the variation in surgical approaches is quantified.

14 Claims, 12 Drawing Sheets

Related U.S. Application Data on Jun. 8, 2021, provisional application No. 63/175,209, filed on Apr. 15, 2021.

(56) References Cited

U.S. PATENT DOCUMENTS

| | | | |
|---|---|---|---|
| 11,205,508 | B2 | 12/2021 | Venkataraman et al. |
| 2015/0044654 | A1 | 2/2015 | Lendvay et al. |
| 2017/0116873 | A1 | 4/2017 | Lendvay et al. |
| 2019/0362834 | A1* | 11/2019 | Venkataraman ....... G06V 20/41 |
| 2024/0153269 | A1 | 5/2024 | Addis et al. |

OTHER PUBLICATIONS

Chao, A., Wang, Y.T. and Jost, L. (2013), "Entropy and the species accumulation curve: a novel entropy estimator via discovery rates of new species". Methods Ecol Evol, 4: 1091-1100. https://doi.org/10.1111/2041-210X.12108 (Year: 2013).*

Chao, A., Shen, TJ. Nonparametric estimation of Shannon's index of diversity when there are unseen species in sample. Environmental and Ecological Statistics 10, 429-443 (2003). https://doi.org/10.1023/A:1026096204727 (Year: 2002).*

Carley et al., "Machine Learning for Surgical Phase Recognition: A Systematic Review", Annals of Surgery, vol. 273, No. 4, Nov. 16, 2020, pp. 684-693.

Ferreira et al., "Approaching Process Mining with Sequence Clustering: Experiments and Findings", Business Process Management, Sep. 2007, 16 pages.

Forestier et al., "Non-Linear Temporal Scaling of Surgical Processes", HAL Open Science, Sep. 2018, 13 pages.

International Search Report and Written Opinion for Application No. PCT/EP2022/060030, International Filing Date: Apr. 14, 2022; Date of Mailing: Jul. 12, 2022; 17 pages.

International Search Report and Written Opinion for Application No. PCT/EP2022/060032, International Filing Date: Apr. 14, 2022; Date of Mailing: Jul. 12, 2022; 17 pages.

Neumuth et al, "Similarity metrics for surgical process models", Artificial Intelligence in Medicine, Oct. 4, 2011, 13 pages.

Cheng et al., "Dual Clustering for Categorization of Action Sequences" 2008 19th International Conference on Pattern Recognition IEEE, 4 pages.

Krishnan et al., "Transition State Clustering: Unsupervised Surgical Trajectory Segmentation for Robot Learning" The International Journal of Robotics; Sage Journals, 2017, pp. 1-24.

\* cited by examiner

Sequences = [[A, B, A], [A, A, A, B, A], [A]]

Average = [A, B, A]

Alignment of average to each sequence by DTW:

Alignment coefficients:

[0,    0,    0]          [2,       0,    0]      [-2,  -2,  -2]

Scaling coefficients:

[0,   -0.66,  -0.66]

QUANTIFYING VARIATION IN SURGICAL APPROACHES

CROSS REFERENCE TO RELATED APPLICATIONS

This application is a National Stage application of PCT/EP2022/060032, filed Apr. 14, 2022, which claims the benefit of U.S. Provisional Patent Application No. 63/297,283, filed Jan. 7, 2022, U.S. Provisional Patent Application No. 63/208,171, filed Jun. 8, 2021, and U.S. Provisional Patent Application No. 63/175,209, filed Apr. 15, 2021 all of which are incorporated by reference in their entirety herein.

BACKGROUND

The present invention relates in general to computing technology and relates more particularly to computing technology for quantifying variations in surgical approaches.

Computer-assisted systems, particularly computer-assisted surgery systems (CASs), rely on video data digitally captured during a surgery. Such video data can be stored and/or streamed. In some cases, the video data can be used to augment a person's physical sensing, perception, and reaction capabilities. For example, such systems can effectively provide the information corresponding to an expanded field of vision, both temporal and spatial, that enables a person to adjust current and future actions based on the part of an environment not included in his or her physical field of view. Alternatively, or in addition, the video data can be stored and/or transmitted for several purposes such as archival, training, post-surgery analysis, and/or patient consultation. The process of analyzing and comparing a large amount of video data from multiple surgical procedures to identify commonalities can be highly subjective and error-prone due, for example, to the volume of data and the numerous factors (e.g., patient condition, physician preferences, etc.) that impact the workflow of each individual surgical procedure that is being analyzed.

SUMMARY

According to an aspect, a system includes a machine learning training system and a data analysis system. The machine learning training system includes one or more machine learning models that are trained to identify a plurality of surgical phases in a video of a surgical procedure. The data analysis system is configured to quantify variation in surgical approaches in a plurality of videos capturing a same type of surgical procedure. The quantifying variation in surgical approaches includes receiving a plurality of surgical videos, each of the plurality of surgical videos capturing a workflow of the same type of surgical procedure. The quantifying also includes segmenting each of the plurality of surgical videos into a segmented workflow that includes a plurality of surgical phases, where the segmenting is based on surgical phases identified by the machine learning training system. The quantifying further includes aligning phases in the segmented workflows to an average workflow of the segmented workflows to create a plurality of aligned workflows, and calculating an entropy for each phase in the aligned workflows based on a Chao-Shen estimator which reduces bias for small sample sizes. The entropy for each phase in the aligned workflows is output to a display device for display. The entropy represents variation in surgical approaches to the surgical procedure.

In addition to one or more of the features described above or below, or as an alternative, further aspects may include that calculating the entropy includes scaling the entropy by its maximum possible value to a value that falls in a specified range of values.

In addition to one or more of the features described above or below, or as an alternative, further aspects may include that the quantifying variation in surgical approaches further includes calculating the average workflow based on the workflows in the plurality of surgical videos.

In addition to one or more of the features described above or below, or as an alternative, further aspects may include that the calculating the average workflow includes analyzing all medoid workflows in the surgical videos and selecting the average workflow from the medoid workflows based on the analyzing.

In addition to one or more of the features described above or below, or as an alternative, further aspects may include that the analyzing includes executing adaptive dynamic time warping-barycenter-averaging (ADBA) using each of the medoid workflows as an initial average.

In addition to one or more of the features described above or below, or as an alternative, further aspects may include that the analyzing is optimized for categoric data and is based at least in part on mode values of phases across the segmented workflows.

In addition to one or more of the features described above or below, or as an alternative, further aspects may include that the optimization includes modifying a length of the average workflow by one of adding a phase to the average workflow or removing a phase from the average workflow.

In addition to one or more of the features described above or below, or as an alternative, further aspects may include that the outputting further includes outputting an indication of a surgical service provider associated with one or more of the aligned workflows to the display device for display.

According to another aspect, a computer-implemented method includes receiving, by a processor, a plurality of surgical videos, each of the plurality of surgical videos capturing a workflow of a same type of surgical procedure and each of the plurality of surgical videos segmented into a segmented workflow that includes surgical phases. A plurality of the segmented workflows are analyzed to calculate an average workflow, and the plurality of the segmented workflows are aligned to the average workflow. Based on the aligning, a variation in the surgical approaches in the plurality of segmented videos is quantified.

In addition to one or more of the features described above or below, or as an alternative, further aspects may include that the analyzing is optimized for categoric data and is based at least in part on mode values of phases across the segmented workflows.

In addition to one or more of the features described above or below, or as an alternative, further aspects may include that the optimization includes modifying a length of the average workflow by one of adding a phase to the average workflow or removing a phase from the average workflow.

In addition to one or more of the features described above or below, or as an alternative, further aspects may include outputting, by the processor to a display device, a graphical representation of the aligned workflows and the variation.

In addition to one or more of the features described above or below, or as an alternative, further aspects may include that the graphical representation identifies a surgical service provider associated with each of the workflows.

In addition to one or more of the features described above or below, or as an alternative, further aspects may include that a scaled entropy value is used to quantify the variation in the surgical approaches.

In addition to one or more of the features described above or below, or as an alternative, further aspects may include that calculating the average workflow includes analyzing all medoid workflows in the surgical videos and selecting the average workflow from the medoid workflows based on the analyzing.

In addition to one or more of the features described above or below, or as an alternative, further aspects may include that the analyzing includes executing ADBA using each of the medoid workflows as an initial average.

According to another aspect, a computer program product includes a memory device having computer-executable instructions stored thereon, which when executed by one or more processors cause the one or more processors to perform operations. The operations include visualizing variations in surgical approaches to performing a surgical procedure. The visualizing includes receiving a plurality of surgical videos, each of the plurality of surgical videos capturing a workflow of a same type of surgical procedure and each of the plurality of surgical videos segmented into a segmented workflow that includes surgical phases. A variation in the workflows in the plurality of surgical videos is quantified and a graphical representation of the quantified variation is output to a display device.

In addition to one or more of the features described above or below, or as an alternative, further aspects may include that the visualizing includes receiving user input via a user interface of the graphical representation, and in response to the user input, outputting to the display device, a second graphical representation that includes additional information describing characteristics of one or both of a service provider or a patient.

In addition to one or more of the features described above or below, or as an alternative, further aspects may include that the graphical representation of the quantified variation includes a graph of the variation over a duration of the surgical procedure.

In addition to one or more of the features described above or below, or as an alternative, further aspects may include that each of the plurality of surgical videos is segmented into surgical phases, and the quantifying is based at least in part on the surgical phases.

Additional technical features and benefits are realized through the techniques of the present invention. Aspects of the invention are described in detail herein and are considered a part of the claimed subject matter. For a better understanding, refer to the detailed description and to the drawings.

BRIEF DESCRIPTION OF THE DRAWINGS

The specifics of the exclusive rights described herein are particularly pointed out and distinctly claimed in the claims at the conclusion of the specification. The foregoing and other features and advantages of the aspects of the invention are apparent from the following detailed description taken in conjunction with the accompanying drawings in which:

Figure 1:
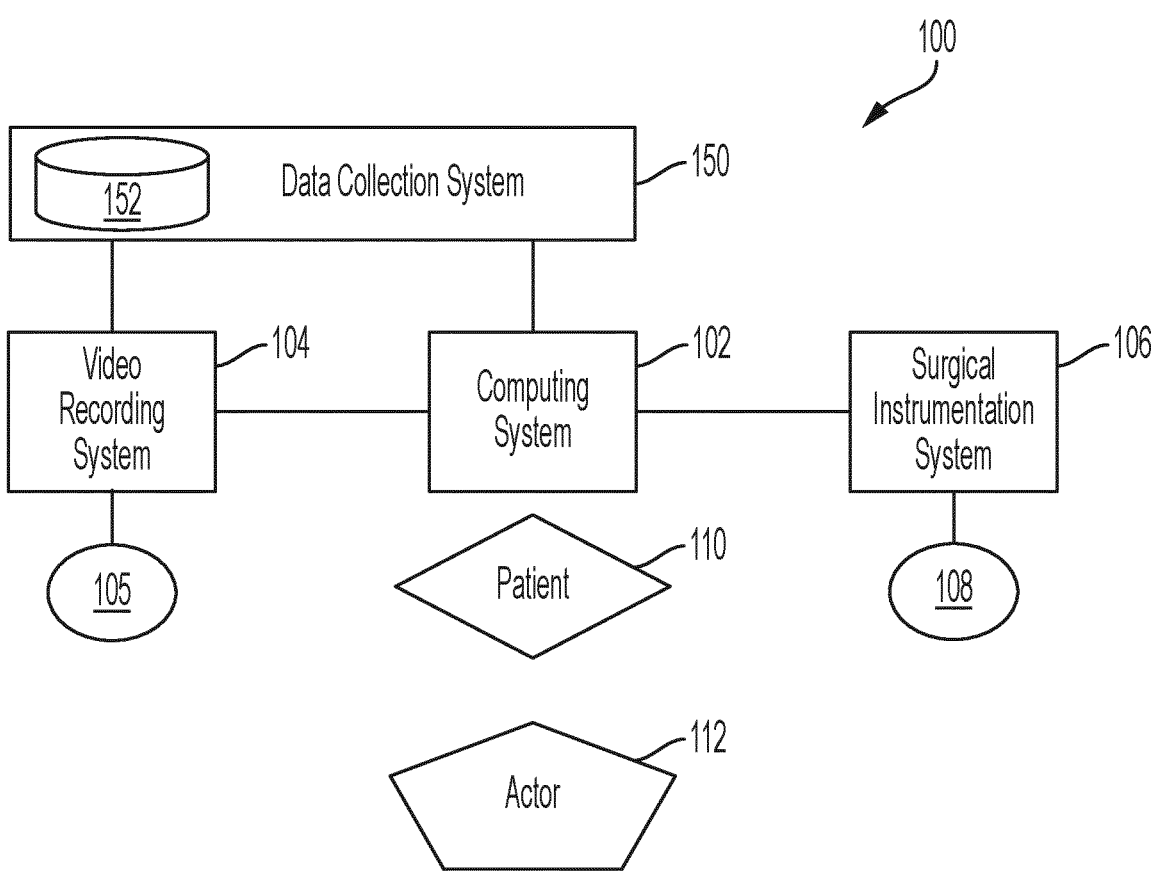
FIG. 1 depicts a computer-assisted surgery (CAS) system according to one or more aspects.

The diagrams depicted herein are illustrative. There can be many variations to the diagrams and/or the operations described herein without departing from the spirit of the invention. For instance, the actions can be performed in a differing order, or actions can be added, deleted, or modified. Also, the term "coupled" and variations thereof describe having a communications path between two elements and do not imply a direct connection between the elements with no intervening elements/connections between them. All of these variations are considered a part of the specification.

DETAILED DESCRIPTION

Exemplary aspects of the technical solutions described herein include systems and methods for quantifying variation in surgical approaches to medical procedures. A key requirement to be able to standardize surgery is the ability to understand and compare surgical variation. Additionally, the capability to quantify variation and identify at what stage in surgery this variation occurs is also an important step towards understanding the relationships between surgical procedure, patient outcomes, and efficiency. One or more aspects of the present invention provide a representative average sequence for a data set, which can easily be compared to other groups and can be used to carry out multiple alignment, and a quantifiable value of variation throughout surgery which can be used to understand surgical standardization. This provides a robust standardization metric that allows adherence to an approach to be measured, and for improvements due to training to be tracked and quantified.

Contemporary approaches use non-linear temporal scaling (NLTS) methods to align a series of surgical workflows and to quantify the variation of the series using entropy. The variation has been used to compare the standard practices in surgery between surgeons at different levels of training to understand the main differences between junior and senior surgeons. NLTS has three main steps: calculation of the average workflow, multiple alignment of the workflows to the average, and calculation of the entropy across the aligned workflows. In contemporary approaches, the average sequences are calculated using dynamic time warping-barycenter-averaging (DBA) and the entropy is calculated using Shannon's entropy. These contemporary methods have been used to identify different standards of surgical practice. However, there are limitations with contemporary approaches due to DBA being designed to be used on workflows of the same length, which is often not the case with surgical workflows. During DBA, the length of the average sequence cannot change, meaning that the initial average chosen at the start will set the length of the final average. This means the final average from the algorithm may not be the best possible average for the data set. As each sequence is aligned to this average sequence, this can have a large impact on the results. In addition, DBA is designed to be used with numerical data rather than categorical data like a surgical phase. Another limitation of contemporary approaches is that the uses of Shannon's entropy can result in bias when applied to small sample sizes because it is based on the probability of each phase occurring. When using a small data set, the observed probability of each phase may be different than its true probability.

Exemplary aspects of the technical solutions described herein follow a similar logic as NLTs and start with the calculation of the average sequence. This average sequence can be used to identify key characteristics of a group, allowing large groups of sequences to be simplified into a single representative sequence. As described herein, the proposed averaging method is based on adaptive DBA (ADBA) which is an improvement over the use of DBA because it is designed to be used on sequences of different lengths. However, ADBA methods were designed to be used on numeric data and one or more aspects of the present invention described herein modify contemporary ADBA methods to work with categorical data, such as surgical phases. In one or more aspects, the average optimization in DBA, average optimization in ADBA, and initialization of both methods are modified. These changes use the medoid sequence, that is the sequence with the smallest sum-of-squares distance when compared to the sequences in the set, as a method to find the "best" average workflow.

In contemporary methods of initializing ADBA, any sequence can be chosen as the initial average, which will then be iteratively optimized. However, when using categorical data (such as surgical phase data), the choice of the initial average impacts the final average. One or more aspects of the present invention address this shortcoming of contemporary approaches by using all medoid sequences from the set as an initial average and the medoid is chosen out of all of the resulting averages.

In contemporary methods of optimization in DBA, the average of each element is found across the set of aligned sequences and the element in the average is updated to have this value. In one or more aspects of the present invention, the mode value is used instead. In the case of multiple modes, an average sequence is generated for each mode value as the element value. The medoid version of the average is then used going forward in the algorithm.

In contemporary methods of optimization in ADBA, elements are inserted or merged in the average sequence, where the value of the new element is the average of the elements on either side of it. In accordance with one or more aspects of the present invention, two average sequences are generated, one where the element has the value of the element to its right and the second with the value of the element to its left. The medoid average out of these two is then chosen and used going forward.

The modifications described above can be used to improve the final average from the modified ADBA, resulting in a final average that is more similar to the sequences in the data set.

In accordance with one or more aspects of the present invention, compact multiple alignment (CMA) is used to align each sequence within the set to the corresponding average sequence. This alignment is carried out on each sequence using dynamic time warping (DTW) with respect to the average. CMA allows multiple phases of the sequence to be aligned to a single phase in the average. Once all the sequences are aligned, they are "unpacked", which includes expanding each sequence so that each phase is only aligned to a single phase. The alignment of the sequences is maintained by inserting repeated values of the previous phase in sequences with no phases to unpack. This prevents any phases from being ignored within sequences due to the alignment, therefore preventing any data loss.

Entropy gives a numerical value of the variation across the set at each point in the surgery based purely on sequencing rather than timing. Contemporary approaches use one of several methods to calculate Shannon's entropy, which is based on the probability of each phase occurring. Previous studies have found that for small sample sizes Shannon's entropy can be biased. One or more aspects of the present invention address the bias issues associated with small sample sizes by using the Chao-Shen estimator of Shannon's entropy which has been found to be efficient for a range of sample sizes. The entropy calculations are scaled by the maximum possible entropy, given the number of sequences and number of possible phases, so that the entropy values are from 0 to 1. This allows the entropy to be directly comparable between groups.

One or more aspects of the present invention also include the calculation of error bands for the entropy calculation to provide insights into the potential errors due to small sample size. These error bands can be calculated using a constant error value that is based on the number of sequences in the set and performed similarly to bootstrapping methods when tested on the data set. This allows a simple calculation to provide an estimate of uncertainty around the entropy calculations, improving the accuracy of comparison between sequence sets of different sizes.

In one example, one or more aspects of the present invention can be utilized to analyze Laparoscopic Roux-en-Y Gastric Bypass surgeries. The averaging method can be used to generate an average workflow for each set of surgeries (e.g., one set from each of several different hospitals). This can be used to identify differences in approaches for Laparoscopic Roux-en-Y Gastric Bypass between the hospitals. Comparison of the average workflows can identify, for example, one hospital of the group using a retro colic approach as standard and the most common approach used at each of the other hospitals. This provides an easily understandable way of comparing the approaches for each hospital. In another example, one or more aspects of the present invention are applied to Laparoscopic Cholecystectomy surgeries and the average workflows may be found based on the assigned grade of the gallbladder, with higher grades resulted in more complex workflows with repetitions of phases showing the increase in complexity of the surgery. The average workflows described herein can allow for easy comparison between groups as well as identification of their key characteristics.

In addition, one or more aspects of the present invention provide multiple alignment of workflows which allows for the possibility of many comparative measures to be calculated. The compact multiple alignment of the surgical workflows based on the average generates a set of aligned sequences of the same length with clear points of similarity and difference. The use of entropy can provide a quantifiable value of variation at each point in the surgery. Due to the scaling of the entropy the calculated values are directly comparable between groups. This can allow the identification of high variation within the surgery and the comparison of variation between hospitals.

Measurable improvement in surgical interventions can be achieved by objectively quantifying surgical standardization, process efficiency and patient outcomes. One or more aspects of the present invention provide a methodology that can effectively achieve this for categorical data, such as surgical phase data. One or more aspects of the present invention improve upon contemporary approaches that use NLTS on surgical phase data by the use of a new, modified ADBA method and the use of the Chao-Shen estimator of Shannon's entropy scaled by its maximum possible value. One or more aspects of the present invention provide a representative average sequence for a data set of surgical workflows, which can easily be compared to other groups (or data sets), and a quantifiable value of variation throughout surgery which can be used to understand surgical standardization. A robust standardization metric, such as that provided by one or more aspects of the present invention described herein allows a surgical approach to be measured and improvements due to training to be tracked and quantified.

In exemplary aspects of the technical solutions described herein, surgical data that is captured by a computer-assisted surgical (CAS) system and segmented into surgical phases is input to the analysis described herein to quantify variation is surgical approaches to a medical procedure.

Turning now to FIG. 1, an example CAS system 100 is generally shown in accordance with one or more aspects. The CAS system 100 includes at least a computing system 102, a video recording system 104, and a surgical instrumentation system 106. As illustrated in FIG. 1, an actor 112 can be medical personnel that uses the CAS system 100 to perform a surgical procedure on a patient 110. Medical personnel can be a surgeon, assistant, nurse, administrator, or any other actor that interacts with the CAS system 100 in a surgical environment. The surgical procedure can be any type of surgery, such as but not limited to cataract surgery, laparoscopic cholecystectomy, endoscopic endonasal transsphenoidal approach (eTSA) to resection of pituitary adenomas, or any other surgical procedure. In other examples, actor 112 can be a technician, an administrator, an engineer, or any other such personnel that interacts with the CAS system 100. For example, actor 112 can record data from the CAS system 100, configure/update one or more attributes of the CAS system 100, review past performance of the CAS system 100, repair the CAS system 100, etc.

A surgical procedure can include multiple phases, and each phase can include one or more surgical actions. A "surgical action" can include an incision, a compression, a stapling, a clipping, a suturing, a cauterization, a sealing, or any other such actions performed to complete a phase in the surgical procedure. A "phase" represents a surgical event that is composed of a series of steps (e.g., closure). A "step" refers to the completion of a named surgical objective (e.g., hemostasis). During each step, certain surgical instruments 108 (e.g., forceps) are used to achieve a specific objective by performing one or more surgical actions.

The video recording system 104 includes one or more cameras 105, such as operating room cameras, endoscopic cameras, etc. The cameras 105 capture video data of the surgical procedure being performed. The video recording system 104 includes one or more video capture devices that can include cameras 105 placed in the surgical room to capture events surrounding (i.e., outside) the patient being operated upon. The video recording system 104 further includes cameras 105 that are passed inside (e.g., endoscopic cameras) the patient 110 to capture endoscopic data. The endoscopic data provides video and images of the surgical procedure.

The computing system 102 includes one or more memory devices, one or more processors, a user interface device, among other components. All or a portion of the computing system 102 shown in FIG. 1 can be implemented for example, by all or a portion of computer system 1100 of FIG. 11. Computing system 102 can execute one or more computer-executable instructions. The execution of the instructions facilitates the computing system 102 to perform one or more methods, including those described herein. The computing system 102 can communicate with other computing systems via a wired and/or a wireless network. In one or more examples, the computing system 102 includes one or more trained machine learning models that can detect and/or predict features of/from the surgical procedure that is being performed or has been performed earlier. Features can include structures such as anatomical structures, surgical instruments 108 in the captured video of the surgical procedure. Features can further include events such as phases, actions in the surgical procedure. Features that are detected can further include the actor 112 and/or patient 110. Based on the detection, the computing system 102, in one or more examples, can provide recommendations for subsequent actions to be taken by the actor 112. Alternatively, or in addition, the computing system 102 can provide one or more reports based on the detections. The detections by the machine learning models can be performed in an autonomous or semi-autonomous manner.

The machine learning models can include artificial neural networks, such as deep neural networks, convolutional neural networks, recurrent neural networks, encoders, decoders, or any other type of machine learning model. The machine learning models can be trained in a supervised, unsupervised, or hybrid manner. The machine learning models can be trained to perform detection and/or prediction using one or more types of data acquired by the CAS system 100. For example, the machine learning models can use the video data captured via the video recording system 104.

Alternatively, or in addition, the machine learning models use the surgical instrumentation data from the surgical instrumentation system 106. In yet other examples, the machine learning models use a combination of video data and surgical instrumentation data.

Additionally, in some examples, the machine learning models can also use audio data captured during the surgical procedure. The audio data can include sounds emitted by the surgical instrumentation system 106 while activating one or more surgical instruments 108. Alternatively, or in addition, the audio data can include voice commands, snippets, or dialog from one or more actors 112. The audio data can further include sounds made by the surgical instruments 108 during their use.

In one or more examples, the machine learning models can detect surgical actions, surgical phases, anatomical structures, surgical instruments, and various other features from the data associated with a surgical procedure. The detection can be performed in real-time in some examples. Alternatively, or in addition, the computing system 102 analyzes the surgical data, i.e., the various types of data captured during the surgical procedure, in an offline manner (e.g., post-surgery). In one or more examples, the machine learning models detect surgical phases based on detecting some of the features such as the anatomical structure, surgical instruments, etc.

A data collection system 150 can be employed to store the surgical data, including the video(s) captured during the surgical procedures. The data collection system 150 includes one or more storage devices 152. The data collection system 150 can be a local storage system, a cloud-based storage system, or a combination thereof. Further, the data collection system 150 can use any type of cloud-based storage architecture, for example, public cloud, private cloud, hybrid cloud, etc. In some examples, the data collection system can use a distributed storage, i.e., the storage devices 152 are located at different geographic locations. The storage devices 152 can include any type of electronic data storage media used for recording machine-readable data, such as semiconductor-based, magnetic-based, optical-based storage media, or a combination thereof. For example, the data storage media can include flash-based solid-state drives (SSDs), magnetic-based hard disk drives, magnetic tape, optical discs, etc.

In one or more examples, the data collection system 150 can be part of the video recording system 104, or vice-versa. In some examples, the data collection system 150, the video recording system 104, and the computing system 102, can communicate with each other via a communication network, which can be wired, wireless, or a combination thereof. The communication between the systems can include the transfer of data (e.g., video data, instrumentation data, etc.), data manipulation commands (e.g., browse, copy, paste, move, delete, create, compress, etc.), data manipulation results, etc. In one or more examples, the computing system 102 can manipulate the data already stored/being stored in the data collection system 150 based on outputs from the one or more machine learning models, e.g., phase detection, structure detection, etc. Alternatively, or in addition, the computing system 102 can manipulate the data already stored/being stored in the data collection system 150 based on information from the surgical instrumentation system 106.

In one or more examples, the video captured by the video recording system 104 is stored on the data collection system 150. In some examples, the computing system 102 curates parts of the video data being stored on the data collection system 150. In some examples, the computing system 102 filters the video captured by the video recording system 104 before it is stored on the data collection system 150. Alternatively, or in addition, the computing system 102 filters the video captured by the video recording system 104 after it is stored on the data collection system 150.

Figure 2:
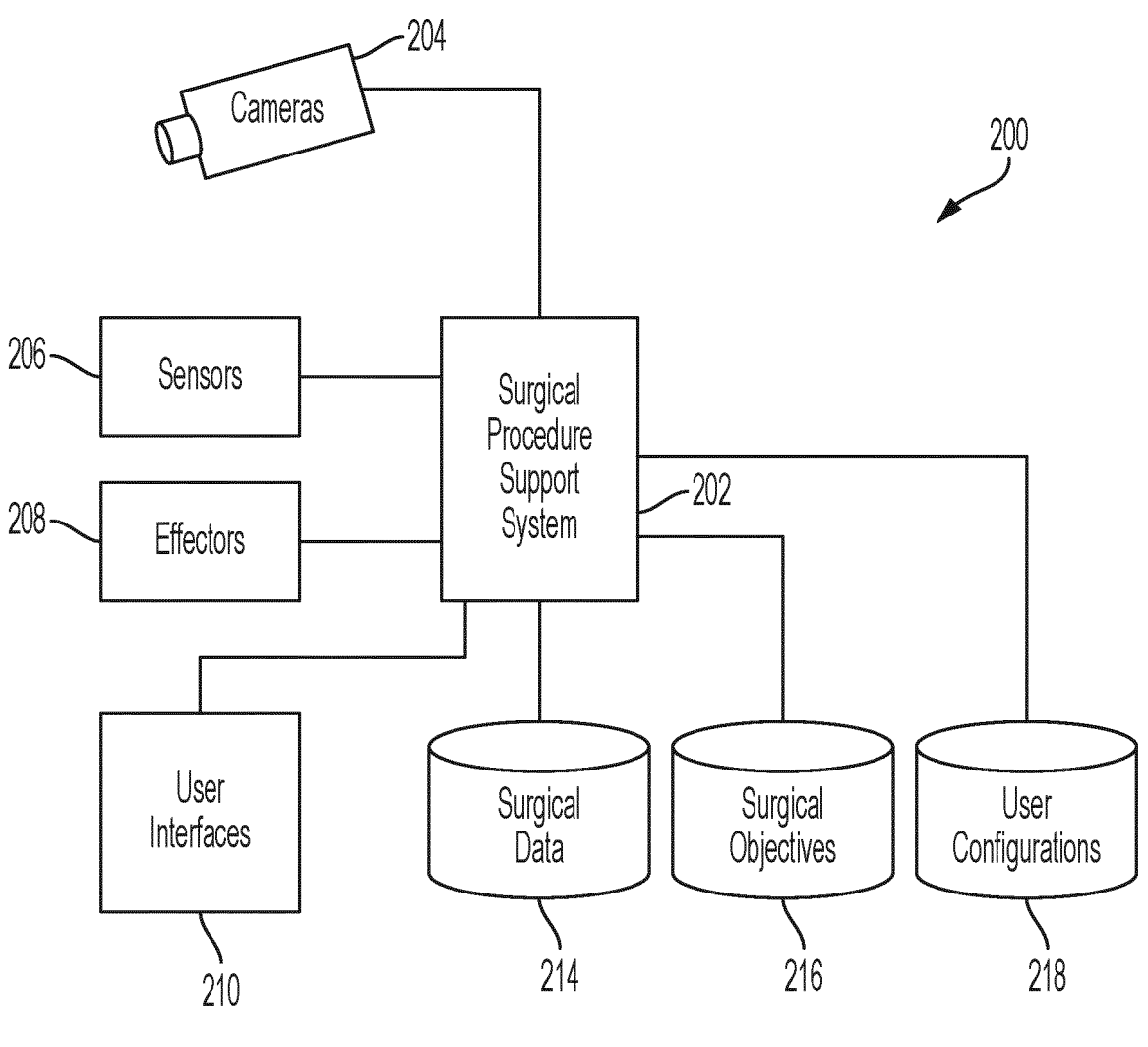
FIG. 2 depicts a surgical procedure system in accordance with one or more aspects.

Turning now to FIG. 2, a surgical procedure system 200 is generally shown in accordance with one or more aspects. The example of FIG. 2 depicts a surgical procedure support system 202 that can include or may be coupled to the CAS system 100 of FIG. 1. The surgical procedure support system 202 can acquire image or video data using one or more cameras 204. The surgical procedure support system 202 can also interface with a plurality of sensors 206 and effectors 208. The sensors 206 may be associated with surgical support equipment and/or patient monitoring. The effectors 208 can be robotic components or other equipment controllable through the surgical procedure support system 202. The surgical procedure support system 202 can also interact with one or more user interfaces 210, such as various input and/or output devices. The surgical procedure support system 202 can store, access, and/or update surgical data 214 associated with a training dataset and/or live data as a surgical procedure is being performed on patient 110 of FIG. 1. The surgical procedure support system 202 can store, access, and/or update surgical objectives 216 to assist in training and guidance for one or more surgical procedures. User configurations 218 can track and store user preferences.

Figure 3:
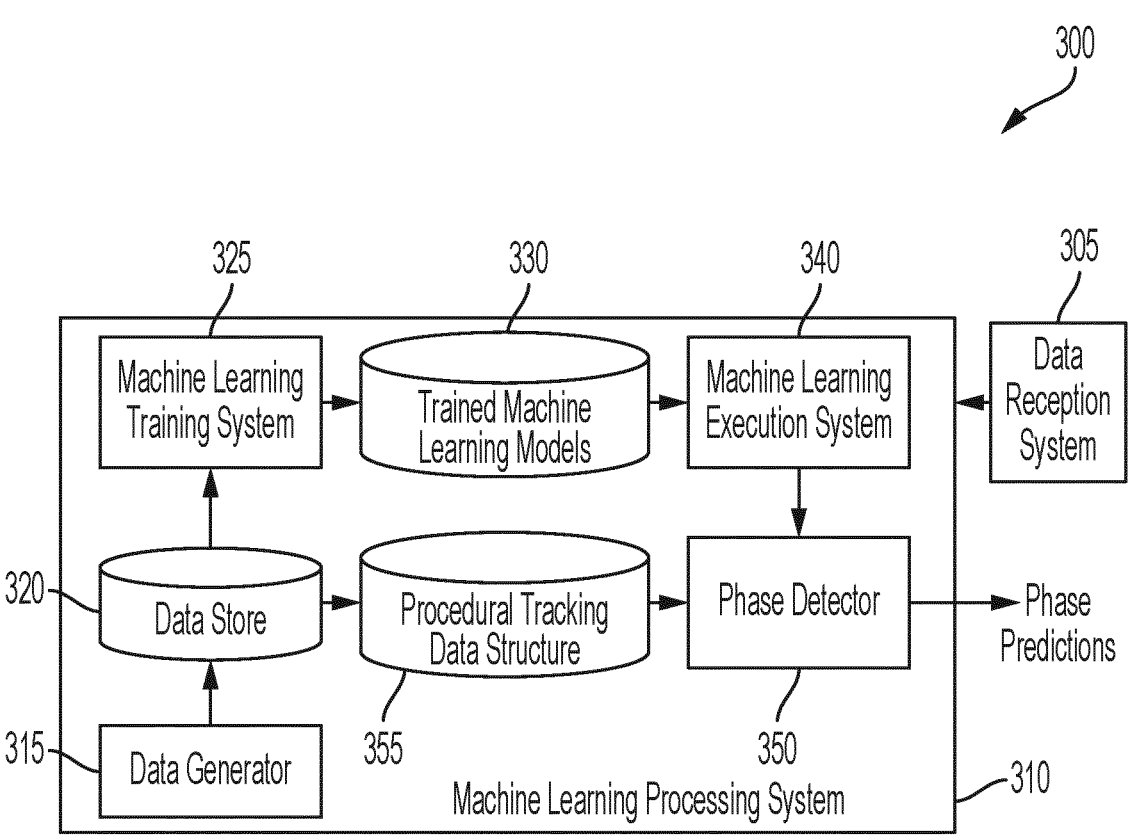
FIG. 3 depicts a system for analyzing video captured by a video recording system according to one or more aspects.

Turning now to FIG. 3, a system 300 for analyzing video and data is generally shown according to one or more aspects. For example, the video and data can be captured from video recording system 104 of FIG. 1. The analysis can result in predicting surgical phases and structures (e.g., instruments, anatomical structures, etc.) in the video data using machine learning. System 300 can be the computing system 102 of FIG. 1, or a part thereof in one or more examples. System 300 uses data streams in the surgical data to identify procedural states according to some aspects.

System 300 includes a data reception system 305 that collects surgical data, including the video data and surgical instrumentation data. The data reception system 305 can include one or more devices (e.g., one or more user devices and/or servers) located within and/or associated with a surgical operating room and/or control center. The data reception system 305 can receive surgical data in real-time, i.e., as the surgical procedure is being performed. Alternatively, or in addition, the data reception system 305 can receive or access surgical data in an offline manner, for example, by accessing data that is stored in the data collection system 150 of FIG. 1.

System 300 further includes a machine learning processing system 310 that processes the surgical data using one or more machine learning models to identify one or more features, such as surgical phase, instrument, anatomical structure, etc., in the surgical data. It will be appreciated that machine learning processing system 310 can include one or more devices (e.g., one or more servers), each of which can be configured to include part or all of one or more of the depicted components of the machine learning processing system 310. In some instances, a part or all of the machine learning processing system 310 is in the cloud and/or remote from an operating room and/or physical location corresponding to a part or all of data reception system 305. It will be appreciated that several components of the machine learning processing system 310 are depicted and described herein. However, the components are just one example structure of the machine learning processing system 310, and that in other examples, the machine learning processing system 310 can be structured using a different combination of the components. Such variations in the combination of the components are encompassed by the technical solutions described herein.

The machine learning processing system 310 includes a machine learning training system 325, which can be a separate device (e.g., server) that stores its output as one or more trained machine learning models 330. The machine learning models 330 are accessible by a machine learning execution system 340. The machine learning execution system 340 can be separate from the machine learning training system 325 in some examples. In other words, in some aspects, devices that "train" the models are separate from devices that "infer," i.e., perform real-time processing of surgical data using the trained machine learning models 330.

Machine learning processing system 310, in some examples, further includes a data generator 315 to generate simulated surgical data, such as a set of virtual images, or record the video data from the video recording system 104, to train the machine learning models 330. Data generator 315 can access (read/write) a data store 320 to record data, including multiple images and/or multiple videos. The images and/or videos can include images and/or videos collected during one or more procedures (e.g., one or more surgical procedures). For example, the images and/or video may have been collected by a user device worn by the actor 112 of FIG. 1 (e.g., surgeon, surgical nurse, anesthesiologist, etc.) during the surgery, a non-wearable imaging device located within an operating room, or an endoscopic camera inserted inside the patient 110 of FIG. 1. The data store 320 is separate from the data collection system 150 of FIG. 1 in some examples. In other examples, the data store 320 is part of the data collection system 150.

Each of the images and/or videos recorded in the data store 320 for training the machine learning models 330 can be defined as a base image and can be associated with other data that characterizes an associated procedure and/or rendering specifications. For example, the other data can identify a type of procedure, a location of a procedure, one or more people involved in performing the procedure, surgical objectives, and/or an outcome of the procedure. Alternatively, or in addition, the other data can indicate a stage of the procedure with which the image or video corresponds, rendering specification with which the image or video corresponds and/or a type of imaging device that captured the image or video (e.g., and/or, if the device is a wearable device, a role of a particular person wearing the device, etc.). Further, the other data can include image-segmentation data that identifies and/or characterizes one or more objects (e.g., tools, anatomical objects, etc.) that are depicted in the image or video. The characterization can indicate the position, orientation, or pose of the object in the image. For example, the characterization can indicate a set of pixels that correspond to the object and/or a state of the object resulting from a past or current user handling. Localization can be performed using a variety of techniques for identifying objects in one or more coordinate systems.

The machine learning training system 325 uses the recorded data in the data store 320, which can include the simulated surgical data (e.g., set of virtual images) and actual surgical data to train the machine learning models 330. The machine learning model 330 can be defined based on a type of model and a set of hyperparameters (e.g., defined based on input from a client device). The machine learning models 330 can be configured based on a set of parameters that can be dynamically defined based on (e.g., continuous or repeated) training (i.e., learning, parameter tuning). Machine learning training system 325 can use one or more optimization algorithms to define the set of parameters to minimize or maximize one or more loss functions. The set of (learned) parameters can be stored as part of a trained machine learning model 330 using a specific data structure for that trained machine learning model 330. The data structure can also include one or more non-learnable variables (e.g., hyperparameters and/or model definitions).

Machine learning execution system 340 can access the data structure(s) of the machine learning models 330 and accordingly configure the machine learning models 330 for inference (i.e., prediction). The machine learning models 330 can include, for example, a fully convolutional network adaptation, an adversarial network model, an encoder, a decoder, or other types of machine learning models. The type of the machine learning models 330 can be indicated in the corresponding data structures. The machine learning model 330 can be configured in accordance with one or more hyperparameters and the set of learned parameters.

The machine learning models 330, during execution, receive, as input, surgical data to be processed and subsequently generate one or more inferences according to the training. For example, the video data captured by the video recording system 104 of FIG. 1 can include data streams (e.g., an array of intensity, depth, and/or RGB values) for a single image or for each of a set of frames (e.g., including multiple images or an image with sequencing data) representing a temporal window of fixed or variable length in a video. The video data that is captured by the video recording system 104 can be received by the data reception system 305, which can include one or more devices located within an operating room where the surgical procedure is being performed. Alternatively, the data reception system 305 can include devices that are located remotely, to which the captured video data is streamed live during the performance of the surgical procedure. Alternatively, or in addition, the data reception system 305 accesses the data in an offline manner from the data collection system 150 or from any other data source (e.g., local or remote storage device).

The data reception system 305 can process the video and/or data received. The processing can include decoding when a video stream is received in an encoded format such that data for a sequence of images can be extracted and processed. The data reception system 305 can also process other types of data included in the input surgical data. For example, the surgical data can include additional data streams, such as audio data, RFID data, textual data, measurements from one or more surgical instruments/sensors, etc., that can represent stimuli/procedural states from the operating room. The data reception system 305 synchronizes the different inputs from the different devices/sensors before inputting them in the machine learning processing system 310.

The machine learning models 330, once trained, can analyze the input surgical data, and in one or more aspects, predict and/or characterize structures included in the video data included with the surgical data. The video data can include sequential images and/or encoded video data (e.g., using digital video file/stream formats and/or codecs, such as MP4, MOV, AVI, WEBM, AVCHD, OGG, etc.). The prediction and/or characterization of the structures can include segmenting the video data or predicting the localization of the structures with a probabilistic heatmap. In some instances, the one or more machine learning models include or are associated with a preprocessing or augmentation (e.g., intensity normalization, resizing, cropping, etc.) that is performed prior to segmenting the video data. An output of the one or more machine learning models can include image-segmentation or probabilistic heatmap data that indicates which (if any) of a defined set of structures are predicted within the video data, a location and/or position and/or pose of the structure(s) within the video data, and/or state of the structure(s). The location can be a set of coordinates in an image/frame in the video data. For example, the coordinates can provide a bounding box. The coordinates can provide boundaries that surround the structure(s) being predicted. The machine learning models 330, in one or more examples, are trained to perform higher-level predictions and tracking, such as predicting a phase of a surgical procedure and tracking one or more surgical instruments used in the surgical procedure.

While some techniques for predicting a surgical phase ("phase") in the surgical procedure are described herein, it should be understood that any other technique for phase prediction can be used without affecting the aspects of the technical solutions described herein. In some examples, the machine learning processing system 310 includes a phase detector 350 that uses the machine learning models to identify a phase within the surgical procedure ("procedure"). Phase detector 350 uses a particular procedural tracking data structure 355 from a list of procedural tracking data structures. Phase detector 350 selects the procedural tracking data structure 355 based on the type of surgical procedure that is being performed. In one or more examples, the type of surgical procedure is predetermined or input by actor 112. The procedural tracking data structure 355 identifies a set of potential phases that can correspond to a part of the specific type of procedure.

In some examples, the procedural tracking data structure 355 can be a graph that includes a set of nodes and a set of edges, with each node corresponding to a potential phase. The edges can provide directional connections between nodes that indicate (via the direction) an expected order during which the phases will be encountered throughout an iteration of the procedure. The procedural tracking data structure 355 may include one or more branching nodes that feed to multiple next nodes and/or can include one or more points of divergence and/or convergence between the nodes. In some instances, a phase indicates a procedural action (e.g., surgical action) that is being performed or has been performed and/or indicates a combination of actions that have been performed. In some instances, a phase relates to a biological state of a patient undergoing a surgical procedure. For example, the biological state can indicate a complication (e.g., blood clots, clogged arteries/veins, etc.), pre-condition (e.g., lesions, polyps, etc.). In some examples, the machine learning models 330 are trained to detect an "abnormal condition," such as hemorrhaging, arrhythmias, blood vessel abnormality, etc.

Each node within the procedural tracking data structure 355 can identify one or more characteristics of the phase corresponding to that node. The characteristics can include visual characteristics. In some instances, the node identifies one or more tools that are typically in use or availed for use (e.g., on a tool tray) during the phase. The node also identifies one or more roles of people who are typically performing a surgical task, a typical type of movement (e.g., of a hand or tool), etc. Thus, phase detector 350 can use the segmented data generated by machine learning execution system 340 that indicates the presence and/or characteristics of particular objects within a field of view to identify an estimated node to which the real image data corresponds. Identification of the node (i.e., phase) can further be based upon previously detected phases for a given procedural iteration and/or other detected input (e.g., verbal audio data that includes person-to-person requests or comments, explicit identifications of a current or past phase, information requests, etc.).

The phase detector 350 outputs the phase prediction associated with a portion of the video data that is analyzed by the machine learning processing system 310. The phase prediction is associated with the portion of the video data by identifying a start time and an end time of the portion of the video that is analyzed by the machine learning execution system 340. The phase prediction that is output can include an identity of a surgical phase as detected by the phase detector 350 based on the output of the machine learning execution system 340. Further, the phase prediction, in one or more examples, can include identities of the structures (e.g., instrument, anatomy, etc.) that are identified by the machine learning execution system 340 in the portion of the video that is analyzed. The phase prediction can also include a confidence score of the prediction. Other examples can include various other types of information in the phase prediction that is output.

It should be noted that although some of the drawings depict endoscopic videos being analyzed, the technical solutions described herein can be applied to analyze video and image data captured by cameras that are not endoscopic (i.e., cameras external to the patient's body) when performing open surgeries (i.e., not laparoscopic surgeries). For example, the video and image data can be captured by cameras that are mounted on one or more personnel in the operating room, e.g., surgeon. Alternatively, or in addition, the cameras can be mounted on surgical instruments, walls, or other locations in the operating room.

Figure 4:
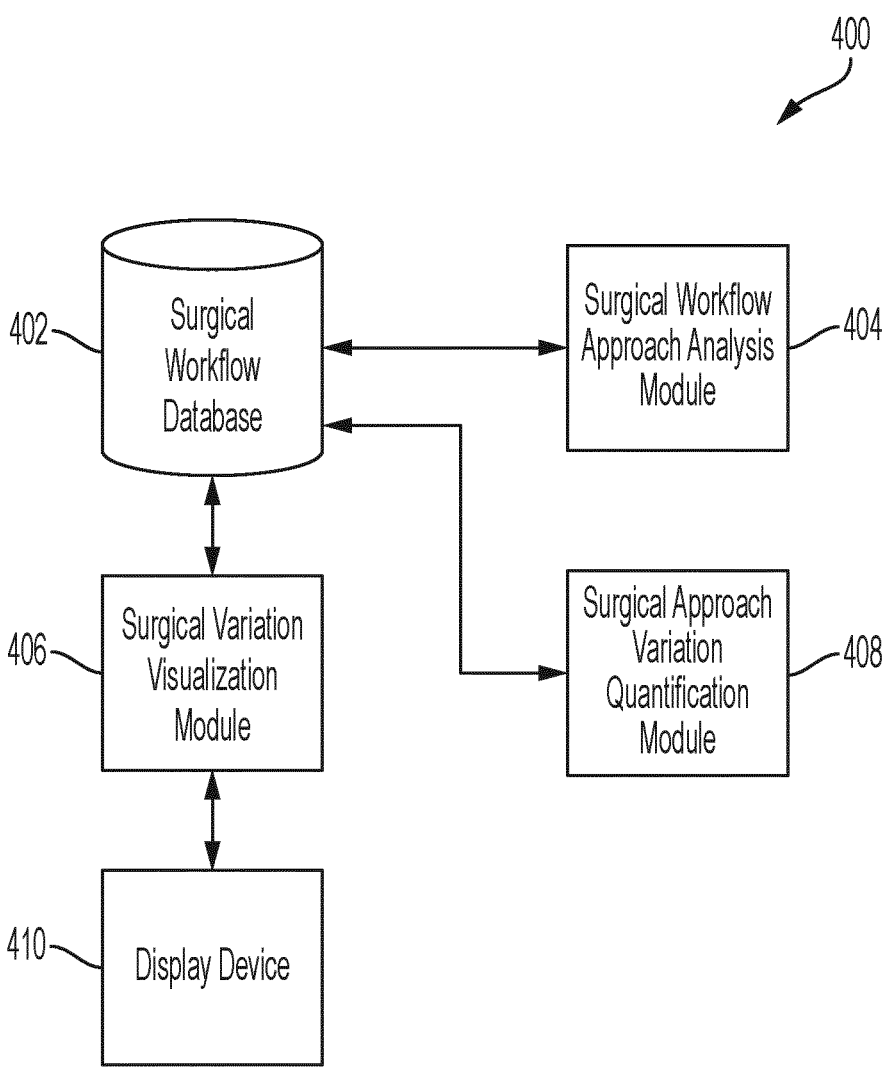
FIG. 4 depicts a block diagram of a data analysis system for quantifying variations in surgical approaches according to one or more aspects.

Turning now to FIG. 4, a block diagram of a data analysis system 400 for quantifying variations in surgical approaches is generally shown in accordance with one or more aspects. All or a portion of data analysis system 400 can be implemented by CAS system 100 of FIG. 1, and/or by computer system 1100 of FIG. 11. The data analysis system 400 shown in FIG. 4 includes surgical workflow database 402, surgical workflow approach analysis module 404, surgical variation visualization module 406, surgical approach variation quantification module 408, and display device 410. Examples of the processing that can be performed by the modules shown in FIG. 4 are shown FIGS. 5-7 and described below.

The surgical workflow database 402 stores video data captured, for example, by video recording system 104 of FIG. 1 and/or cameras 204 of FIG. 2, which is broken into phases, for example, by machine learning processing system 310 of FIG. 3. According to aspects of the technical solutions described herein, the surgical workflow database 402 is located in a storage device 152 of the data collection system of FIG. 1 or stored as surgical data 214 of FIG. 2. The surgical workflow database 402 includes surgical video data recorded during several iterations of the same medical procedure by one or more different surgical service providers. The display device 410 shown in FIG. 4 can be implemented by any user display device that is accessible to a user who has been granted access to viewing the results of the analysis described herein. Aspects include the display device 410 supporting a graphical user interface (GUI) for outputting graphical data.

All or a portion of the surgical workflow approach analysis module 404, surgical approach variation quantification module 408, and surgical variation visualization module 406 can be implemented by computer instructions being executed by computing system 102 of FIG. 1. Surgical workflow approach analysis module 404 receives surgical workflow data, from the surgical workflow database 402, that includes video recordings of multiple surgical procedures of the same type and creates groupings of similar workflows. The video recording, or surgical workflow, of each instance of the particular type of surgical procedure is annotated with phases that have been identified, for example, by machine learning processing system 310 and/or via manual annotation. The annotation can be used to segment a surgical workflow into surgical phases. Further, the surgical workflows are grouped/clustered automatically using machine learning techniques. The grouping can be performed based on one or more factors. The factors can include, for example, but are not limited to, the identified surgical phases in each surgical workflow, medical personnel (e.g., surgeon, staff, trainee/interns, etc.) performing the surgical workflow, hospital/institution where the surgical workflow is being performed, equipment used for the surgical workflow, etc. or a combination thereof. The surgical approach variation quantification module 408 calculates and assigns an entropy value to a group of surgical workflows to indicate, or to quantify, the variation in the surgical approaches in the group. The entropy value and an identifier of the group of surgical workflows can be stored in the surgical workflow database 402 along with pointers to surgical workflows belonging to each group.

The surgical variation visualization module 406 shown in FIG. 4 can provide authorized users with different views via display device 410 of the analysis of the data stored in the surgical workflow database 402. For example, each grouping can be shown in a different color, or surgical workflows capturing surgeries by different surgical service providers can be shown in different colors. Examples are shown below in FIGS. 8-10. In one or more aspects of the present invention, all, or a portion, of the surgical variation visualization module 406 is executing by a processor located on a user device (e.g., a personal computer, laptop, mobile phone, etc.) and the display device 410 is located on or attached to the user device. All or portion of the surgical workflow database 402 can be accessed by the surgical variation visualization module 406 via one or more network connections.

The computing environment of FIG. 4 may be implemented with any appropriate logic, wherein the logic, as referred to herein, can include any suitable hardware (e.g., a processor, an embedded controller, or an application specific integrated circuit, among others), software (e.g., an application, among others), firmware, or any suitable combination of hardware, software, and firmware, in various aspects.

It is to be understood that the block diagram of FIG. 4 is not intended to indicate that system 400 is to include all of the components shown in FIG. 4. Rather, the system 400 can include any appropriate fewer or additional components not illustrated in FIG. 4, such as but not limited to one or more additional display devices 410 and/or surgical workflow databases 402. In addition, the components shown in FIG. 4 may be arranged differently. For example, the surgical workflow approach analysis module 404 and the surgical approach variation quantification module 408 may be located on different computer servers, or they may be part of the same processing unit.

Figure 5:
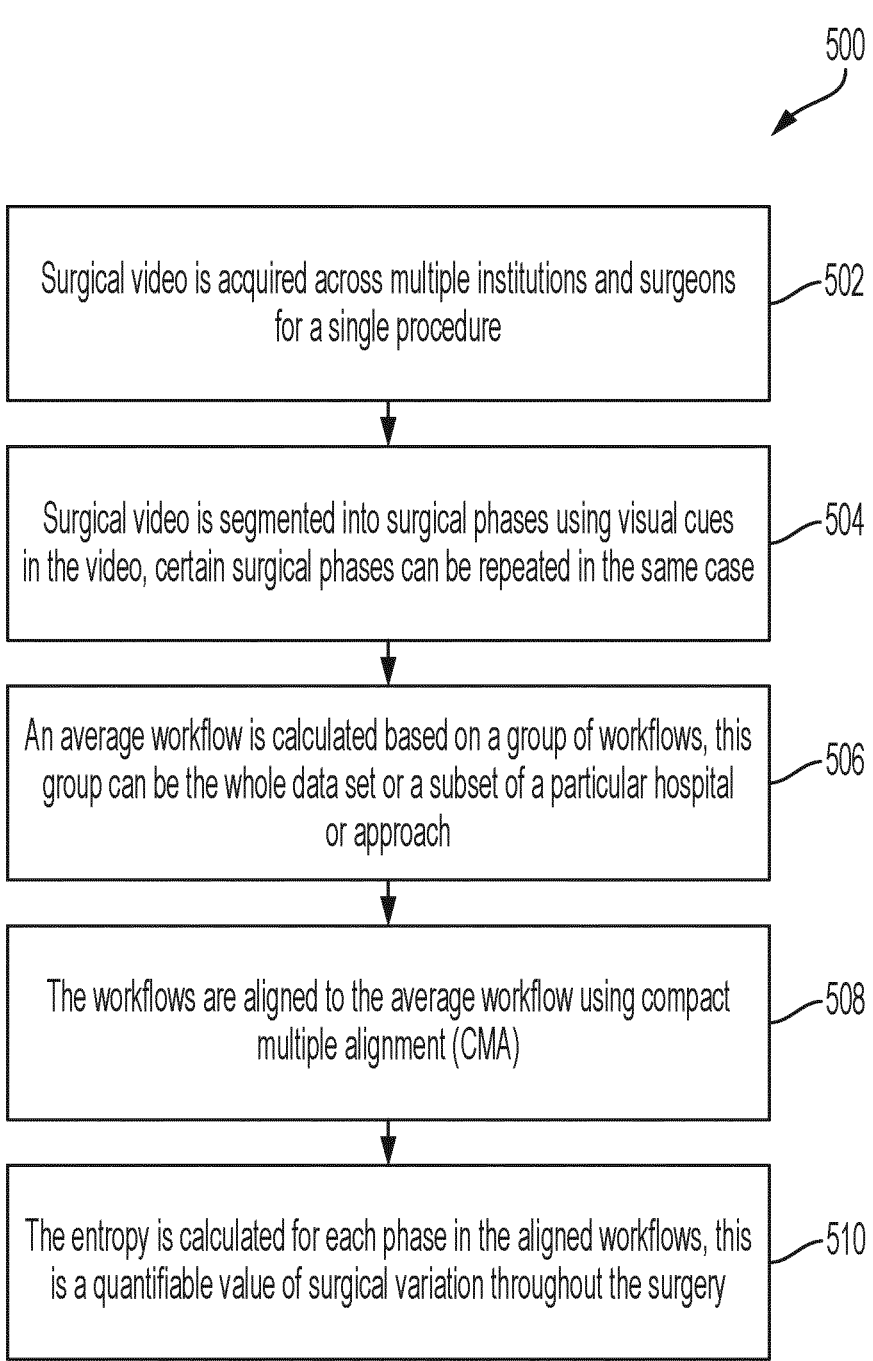
FIG. 5 depicts a flowchart of a method for quantifying variations in surgical approaches according to one or more aspects.

Turning now to FIG. 5, a flowchart of a method 500 for quantifying variations in surgical approaches is generally shown in accordance with one or more aspects. All or a portion of method 500 can be implemented, for example, by all or a portion of CAS system 100 of FIG. 1, system 200 of FIG. 2, system 300 of FIG. 3, and/or system 400 of FIG. 4. Method 500 shown in FIG. 5 includes a pipeline that can be used to quantify variations in surgical approaches.

The method 500 shown in FIG. 5 uses NLTS methods to extract an average sequence from a set, or data set, of surgical phase sequences (workflows). This average can be used to identify the key characteristics of a data set and to easily compare differences in workflow between different groups (e.g., of hospitals, doctors, patients, etc.). The average can also be used to align all of the workflows into a comparable format. The ability to perform multiple alignment allows for the possibility of many comparative measures to be calculated. The method 500 shown in FIG. 5 also calculates entropy which is used to quantify the surgical variation in the workflows within the set, throughout the surgery.

Surgical workflow data (e.g., surgical video) is acquired or received, at block 502 of FIG. 5. At least a portion of the surgical workflow data can be acquired, for example, from data collection system 150 of FIG. 1. The acquired surgical workflow data pertains to a single type of surgical procedure or a group of similar procedures, and may include workflow data from multiple surgical service providers such as multiple different surgeons and/or multiple institutions (e.g., hospitals) and by different surgeons. The surgical workflow data includes video data, e.g., laparoscopic video, for each iteration of the surgical procedure. The dataset acquired at block 502 can include additional data for each surgical procedure, such as but not limited to hospital identification/ characteristics (e.g., location, frequency of performing the surgical procedure, etc.), surgeon identification/characteristics (e.g., years in practice, training, experience with the surgical procedure, etc.), and/or patient identification/characteristics (e.g., age, height, weight, etc.).

At block 504, the surgical video is segmented into surgical phases using, for example, visual cues in the video. For example, the visual cues can include but are not limited to surgical instruments, anatomical approaches, etc., in the video. The segmenting can include annotating the video and breaking the video up into multiple segments based on the annotating. According to aspects of the technical solutions described herein, the duration of the segments can also be used to identify surgical approaches. In addition, certain surgical phases can be repeated in the same case.

As used herein, the term "case" refers to one iteration of the surgical procedure, that is, a single surgery represented by a single surgical workflow. The surgical workflow data, or dataset, acquired at block 502 can include several cases (hundreds or even thousands) of a particular type of surgical procedure obtained from different surgical service providers. The surgical workflow data can also be obtained for a single surgical service provider to analyze consistency and/or approaches used by the single surgical service provider.

At block 506 of FIG. 5, an average workflow, or sequence, is calculated based on a group of workflows. This group can be the whole data set or a subset that includes a particular hospital, a particular surgical approach, or a patient having particular characteristics. In accordance with one or more aspects of the present invention, the calculation of the average sequence is based on ADBA with a modification that allows ADBA to be applied to categoric rather than numerical data. ADBA is an iterative process that identifies whether the average sequence is too long or too short compared to the sequences in the set, and it inserts or removes elements accordingly. The values of the elements chosen for insertion or removal are based on the mode values in the surgeries in the set. This results in an average workflow that is as similar to all the sequences in the set as possible. Average workflows can be used to reduce a set of multiple different workflows into one workflow that is easily understandable and comparable.

A simplified example includes five surgical workflows or cases, each segmented into a plurality of phases. "A", "B", "C", and "D" each represent a different phase of a surgical procedure. As shown below, Surgical Workflow 0 is segmented (e.g., at block 504 of FIG. 5) into an ordered sequence of phases that includes "ABCDADB." "ABCDADB" is a symbolic representation of Surgical Workflow 0.

In this example, the phases include phases A, B, C, and D and the sequences follow:

Surgical Workflow 0: A B C D A B D,
Surgical Workflow 1: A B C B D A B D,
Surgical Workflow 2: A B C B A B D,
Surgical Workflow 3: D A D B A B C, and
Surgical Workflow 4: D A D C B A B C.

Using ADBA, the average of these sequences, or workflows, is the same as Surgical Workflow 2: A B C B A B D.

For the first six elements of the average, the phase in the average is the mode of the elements in the set of sequences. For the first element in each of the sequences the mode phase is A, the second is B, the third C, the fourth B, the fifth and the sixth B. The final element of the average is phase D, which is the most common last element in the set of elements. The sequences are different lengths, which is why the average phase is not necessarily the mode element near the end as the alignment using DTW has shifted the end points of the sequences relative each other. Exemplary processes for calculating the average workflow are described below in reference to FIG. 6 and FIG. 7.

Once the average workflow is calculated, processing continues at block 508 of FIG. 5, with aligning the work-flows to the average workflows using compact multiple alignment (CMA). CMA is used to align each sequence within the set to the corresponding average sequence. This alignment is carried out on each sequence using DTW with respect to the average. CMA allows multiple phases of the sequence to be aligned to a single phase in the average. Once all the sequences are aligned, they are "unpacked" which includes expanding each sequence so that each phase is only aligned to a single phase in the average sequence. The alignment of the sequences is maintained by inserting repeated values of the previous phase in sequences with no phases to unpack. This prevents any phases from being ignored within sequences due to the alignment therefore preventing any data loss.

Referring back to the example, each sequence is aligned to the average sequence using DTW which results in the following aligned sequences:

Surgical Workflow 0: A A B C D DA B D,
Surgical Workflow 1: A A B C B D A B D,
Surgical Workflow 2: A A B C B B A B D,
Surgical Workflow 3: D D A D B B A B C, and
Surgical Workflow 4: D A D C B B A B C.

The order of the sequences has not changed, additional phases have just been added in where necessary, for the alignment to be carried out. This addition of phases is part of the unpacking process used to align each sequence.

At block 510, the entropy is calculated for each phase in the aligned workflows. The calculated entropy includes a quantifiable value of surgical variation throughout the sur-gery. In accordance with one or more aspects of the present invention, the entropy at each element of the aligned sequences is calculated based on the Chao-Shen estimator for Shannon's entropy. Shannon's entropy is based on the probability that each phase will occur in an element. For each element the occurrence of each phase is found, for the above the occurrence of the phases in the first element is 3, 0, 0, 2 for phases A, B, C, D respectively. These counts of each phase are used to calculate the entropy for each element in the sequences. Entropy is calculated using the Chao-Shen estimator, this takes the count of how often each phase occurs in the sequence sets e.g. 2 and 3 for the first element in the example above for D and A phases respectively. The probability of these phases occurring is 2/5 and 3/5 respec-tively. The good Turing frequencies are calculated using the following formulas: n=the number of phase counts, m=the number of phase counts with a value of 1 unless all phases counts are 1 then m=n−1, C=1−m/n. The good Turing frequencies are the initial probability of the phases multi-plied by C. For the above example m=0 as no phase counts are 1, therefore C=1 and the good Turing frequencies are 2/5 and 3/5. The Chao-Shen estimator is then calculated based on the good Turing frequencies (gtf). For each phase count the entropy=gtf*ln(gtf)/1−(1−gtf)^n. The total entropy is the sum of the entropy for each phase count multiplied by −1. For the above example the entropy for phase D, with a gtf=2/3 is −0.3974 and for phase A, with a gtf=3/5 is −0.3097. This gives a total entropy of 0.7071 for the first element in the sequences. This is then scaled by the maxi-mum possible entropy based on the number of sequences and number of possible phases. For the previous example there are 5 sequences in the set and a total of 4 possible phases (all phases that occur within any of the sequences). The maximum entropy will occur when there is an equal split in counts, or as equal as possible, between each of the possible phases. For the above example this would be counts of 2, 1, 1 and 1 for the four phases. The Chao-Shen estimator is then carried out for the counts that would result in the maximum entropy giving a value of 2.2821 for the maxi-mum possible entropy. Dividing 0.7071 by 2.2821 gives a value of 0.31 as the scaled entropy for the first element in the example.

Referring to the example, the entropy of the first element in the aligned sequences is 0.31 (the first element has 2 Ds and 3 As), the entropy the first, the entropy of the second element is 0.35 (4 As and 1 D), the entropy of the third element is 0.65 (1 D, 1 A, and 3 Bs), the entropy of the fourth element is 0.35 (1D and 4 Cs), the entropy of the fifth element is 0.35 (1D and 4 Bs), the entropy of the sixth element is 0.31 (3 Bs and 2 Ds), the entropy of the seventh element is 0 (5 As), the entropy of the eighth element is 0 (5 Bs), and the entropy of the ninth element is 0.35 (2 Cs and 3 Ds). These values can be presented to a user, for example in any graphical form such as that shown in FIG. 10 below, or in any other format.

An entropy value of 0 is assigned to elements seven and eight where all sequences have the same phase. A value of 1 would relate to the maximum possible entropy given the number of sequences and possible phases. In the example, the entropy is highest in element 3, which has the most different phases out of the whole surgery.

The processing shown in FIG. 5 is not intended to indicate that the operations are to be executed in any particular order or that all of the operations shown in FIG. 5 are to be included in every case. Additionally, the processing shown in FIG. 5 can include any suitable number of additional operations.

Figure 6:
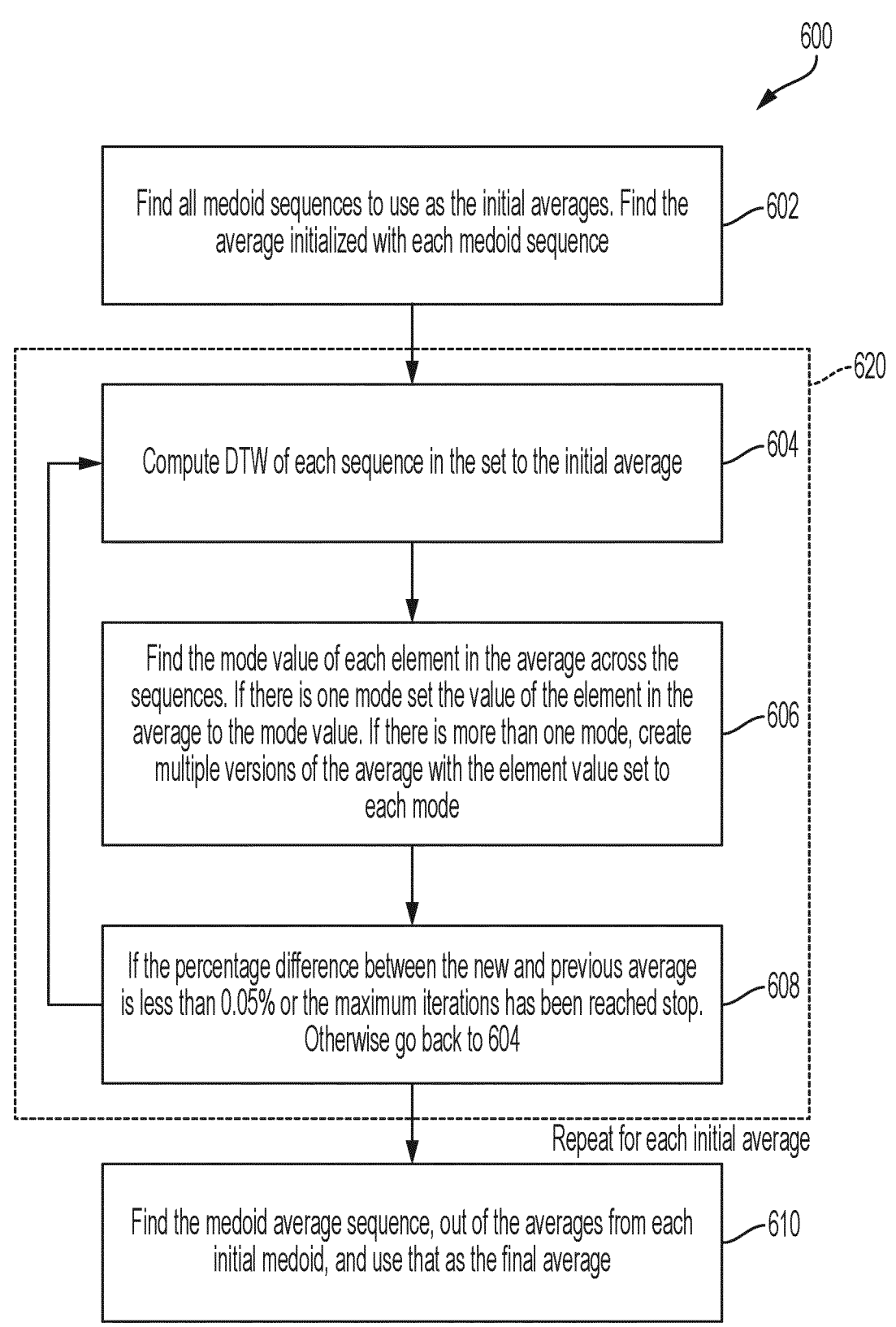
FIG. 6 depicts a flowchart of a method for performing dynamic time warping-barycenter-averaging (DBA) according to one or more aspects.

Turning now to FIG. 6, a flowchart of a method 600 for performing DBA is generally shown in accordance with one or more aspects. All or a portion of method 600 can be implemented, for example, by all or a portion of CAS system 100 of FIG. 1, system 200 of FIG. 2, system 300 of FIG. 3, and/or system 400 of FIG. 4.

One or more aspects of the present invention alter the way that the DBA initializes and updates the average sequence are performed when compared with contemporary DBA methodologies. Contemporary methods of applying DBA specify that any sequence can be used for initialization, however, with categoric data (such as surgical phases) the initial average that is chosen impacts the final outcome. To account for this, one or more aspects of the present invention find all medoid sequences and then the DBA is run using each medoid as the initial average. The best average, the medoid, is then chosen at the end as the final average.

At block 602 of FIG. 6, all medoid sequences in the data set are located to use as the initial averages. Block 620, which includes blocks 604, 606, and 608 is then performed for each of the initial averages. This block optimizes the initial average by iteratively updating the average to the mode values of the aligned sequences. This is repeated until the iterations have reached a maximum value or there is a minimal change in the average in the last iteration. This block is repeated for each medoid sequence within the set. A DTW of each sequence in the set to the initial average is computed at block 604. The mode value of each element in the average across the sequences is found at block 606. If there is one mode, the value of the element in the average is set to the mode value. If there is more than one mode, then multiple versions of the average are created with the element value set to each mode. At block 608, if the percentage difference between the new and previous average is less than a predefined value (e.g., 0.05%, 0.1%, 0.01%, etc.) or the maximum number of iterations has been reached then processing continues at block 610. Otherwise, processing continues at block 604 to perform another iteration. At block 610, the medoid average sequence, out of the averages from each initial medoid is located and used as the final average. In this manner, the medoid of these averages when compared to the set of sequences is found and that average is used going forward in the algorithm.

The processing shown in FIG. 6 is not intended to indicate that the operations are to be executed in any particular order, or that all of the operations shown in FIG. 6 are to be included in every case. Additionally, the processing shown in FIG. 6 can include any suitable number of additional operations.

In contemporary approaches the average is updated by finding the barycenter average of each element based on the sequences in the set. However, this is not possible with categoric data. Therefore, in one or more aspects of the present invention, the mode value is found for each element. In the case of multiple modes different averages are created, one with each mode as the element value. The best average, the medoid, is then found and used going forward.

For example, for a set of sequences:

A, A, C, D, E
A, B, B, D, E
A, B, B, D, E
A, A, C, D, E

The modes of each element are as follows: A, A or B, C or B, D, E

The averages combining each of the potential modes include:

A, A, C, D, E
A, B, C, D, E
A, A, B, D, E
A, B, B, D, E

Figure 7:
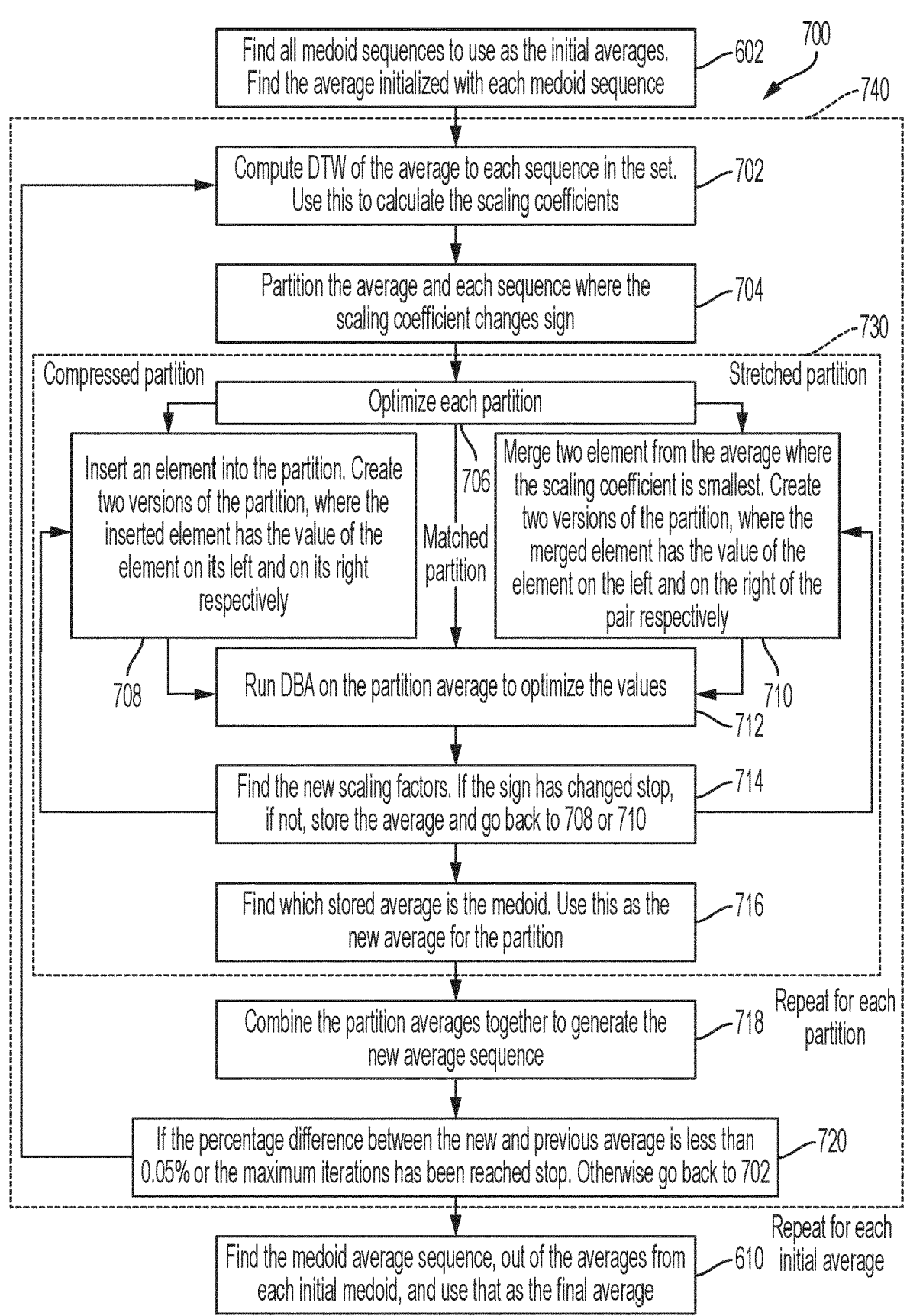
FIG. 7 depicts a flowchart of a method for performing adaptive DBA (ADBA) according to one or more aspects.

Turning now to FIG. 7, a flowchart of a method 700 for performing adaptive DBA (ADBA) is generally shown in accordance with one or more aspects. All or a portion of method 700 can be implemented, for example, by all or a portion of CAS system 100 of FIG. 1, system 200 of FIG. 2, system 300 of FIG. 3, and/or system 400 of FIG. 4.

Similar to method 600 of FIG. 6, the method 700 shown in FIG. 7 finds and uses all medoid sequences as the initial average and the best final average is selected and used as the output. The optimization of the average partitions includes either inserting a new element or merging two elements to change the length of the partition. In contemporary ADBA methods, the new inserted element has an initial value of the average of the elements on either side of it. When the two elements are merged, the resulting element has a value of the average of the merged elements. These methods of averaging values are not possible when using categorical data such as surgical phases. One or more aspects of the present invention accommodate categorical data by creating two potential averages in both these situations. One where the new element has the value of the element on its right, the other where it has the value of the element on its left. The best average, the medoid, is then found and used in the algorithm going forward.

A simple example includes an average sequence of:

A, B, C, D, E

If an element is to be inserted between B and C the two potential averages are:

A, B, B, C, D, E
A, B, C, C, D, E

In accordance with one or more aspects of the present invention, the best version of these two sequences, the medoid, will be used going forward.

Turning now to FIG. 7, at block 602 all medoid sequences are located to use as the initial averages. Processing continues at block 740, which includes blocks 702-720, and is performed for each initial average. This block carries out optimization of the initial average and is carried out for each possible medoid sequence. The average is optimized by splitting it into partitions, where each partition is either too short when aligned by DTW to the sequences or too long. Each partition is then optimized and joined together to provide an updated average sequence. This is iterated until the maximum iterations have been reached or there is minimal change in the average.

Figure 12:
FIG. 12 depicts a block diagram of an alignment process according to one or more aspects.
Figure 12:
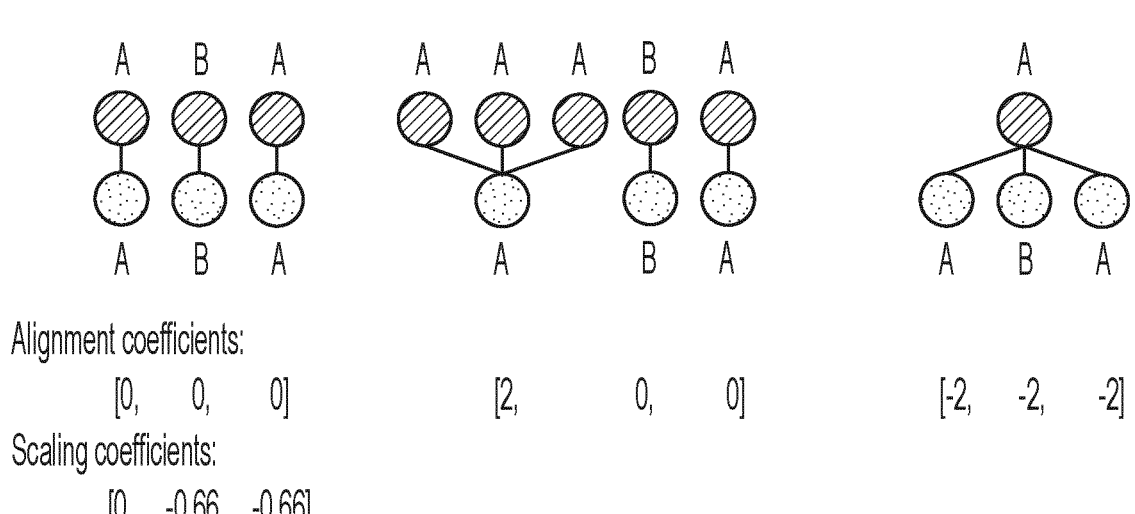

At block 702, the DTW of the average to each sequence in the set is computed. The average is used to calculate the scaling coefficients. The scaling coefficients are a value for each element in the average which represents whether on average the element was matched to multiple elements in the sequences or vice versa. This gives an indication of whether the average is too long or too short at this point in comparison to the sequences. When the average is aligned using DTW to a sequence the alignment coefficient is calculated for each element in the average; 0 if the element is matched to one element in the sequence, if it is matched to multiple elements in the sequence it is given a value of the number of elements it is matched to $-1$, or 1—the number of elements in the average matched to one element in the sequence. The scaling coefficients are then the sum of the alignment coefficients for each element for the average when aligned to each sequence in the set. For example, as shown in the block diagram 1200 of FIG. 12 which depicts an alignment of the following example, for a sequences ABA, AAABA and A and an average sequence of ABA. ABA aligned to the first sequence would result in alignment coefficients 0, 0 and 0 as each element in the average would be matched to one in the sequence. For the second sequence the first element of the average, A, would be matched to the first 3 elements in the sequence AAA giving an alignment coefficient of $3-1=2$. The following elements would be matched to one element in the sequence giving alignment coefficients of 2, 0 and 0. For the final sequence all 3 elements of A would be matched to the only element of the sequence giving alignment coefficients of $-2$, $-2$ and $-2$. The scaling coefficients are the sum of the alignment coefficients of each element. These would be 0 (0+2-2), $-2$ (0+0-2), $-2$ (0+0-2). These values are then scaled by the number of total elements, 3 in this case giving alignment coefficients 0, $-0.66$, $-0.66$. This indicates that the average is generally too long when compared to the sequences in the last two elements. A positive value would indicate the opposite.

Processing continues at block 704 with partitioning the average and each sequence where the scaling coefficient changes sign. The partitioning includes separating the average sequence into sections, or partitions, where each section is either too long or too short when compared to the sequences. For example, for an average ABCDE with scaling coefficients $-1,0,-2,2,3$ the average would be split into two partitions ABC and DE, the first being too long and the second being too short when compared to the sequences. Each partition will then be optimized differently by merging elements in partitions that are too long and inserting elements in partitions that are two short.

Processing continues at block 730 which is repeated for every partition created in block 704. This block optimizes each partition within the average by either inserting or merging elements within the partition and then carrying out DBA. This is repeated for each partition until the scaling coefficient of the partition has changed sign. The processing performed in block 730 includes blocks 706-716. At block 706, depending on the type of partition i.e., too long (negative scaling coefficients), too short (positive scaling coefficients) or matched (scaling coefficients of 0) a different optimization procedure will be carried out. For a partition that is the same size as the average sequence, processing continues at block 712. Alternatively, for a partition that is too short when compared to the sequences, block 708 is performed to insert an element into the partition. This includes creating two versions of the partition, one version where the inserted element has the value of the element on its left and another version where the inserted element has the value of the element on its right. Alternatively, for a partition that that too long when compared to the sequences, block 710 is performed to merge two elements from the average where the scaling partition is smallest. Two versions of the partition are created at block 710, one where the merged element has the value of the element to on the left and another where the merged element has the value of the element on the right.

At block 712, DBA, such as DBA method 600 of FIG. 6, is run on the partition average to optimize the values. This involves optimizing the values of the partition average based on the mode values of the corresponding partitions of the sequences. Processing continues at block 714 with finding the new scaling factors as explained previously. If the sign of the scaling factors has changed the processing continues at block 716. Otherwise, if the sign of the scaling factors has not changed, the average is stored, and processing returns to block 708 or 710. At block 716, the stored average which is the medoid is used as the new average for the partition. Once the processing in block 730 is repeated for every partition, processing continues at block 718 with concatenating the partition averages together to generate the new average sequence and processing continues at block 720.

At block 720, if the percentage difference between the new and previous average is less than a predefined value (e.g., 0.05%, 0.1%, 0.01%, etc.) or the maximum number of iterations has been reached then processing continues at block 610. Otherwise, processing continues at block 702 to perform another iteration. At block 610, the medoid average sequence, out of the averages from each initial medoid is located and used as the final average. In this manner, the medoid of these averages when compared to the set of sequences is found and that average is used going forward in the algorithm.

In accordance with one or more aspects, there are a few times in the algorithm that an average sequence is chosen from a list by selecting the medoid one (the optimization sections in DBA and ADBA and at the end of the algorithm). In the case that there is more than one medoid, the sequence with the lowest Levenshtein distance when compared to the data set is used. This is a common distance measure when comparing two lists of letters, as our phase data is.

The processing shown in FIG. 7 is not intended to indicate that the operations are to be executed in any particular order, or that all of the operations shown in FIG. 7 are to be included in every case. Additionally, the processing shown in FIG. 7 can include any suitable number of additional operations.

Figure 8:
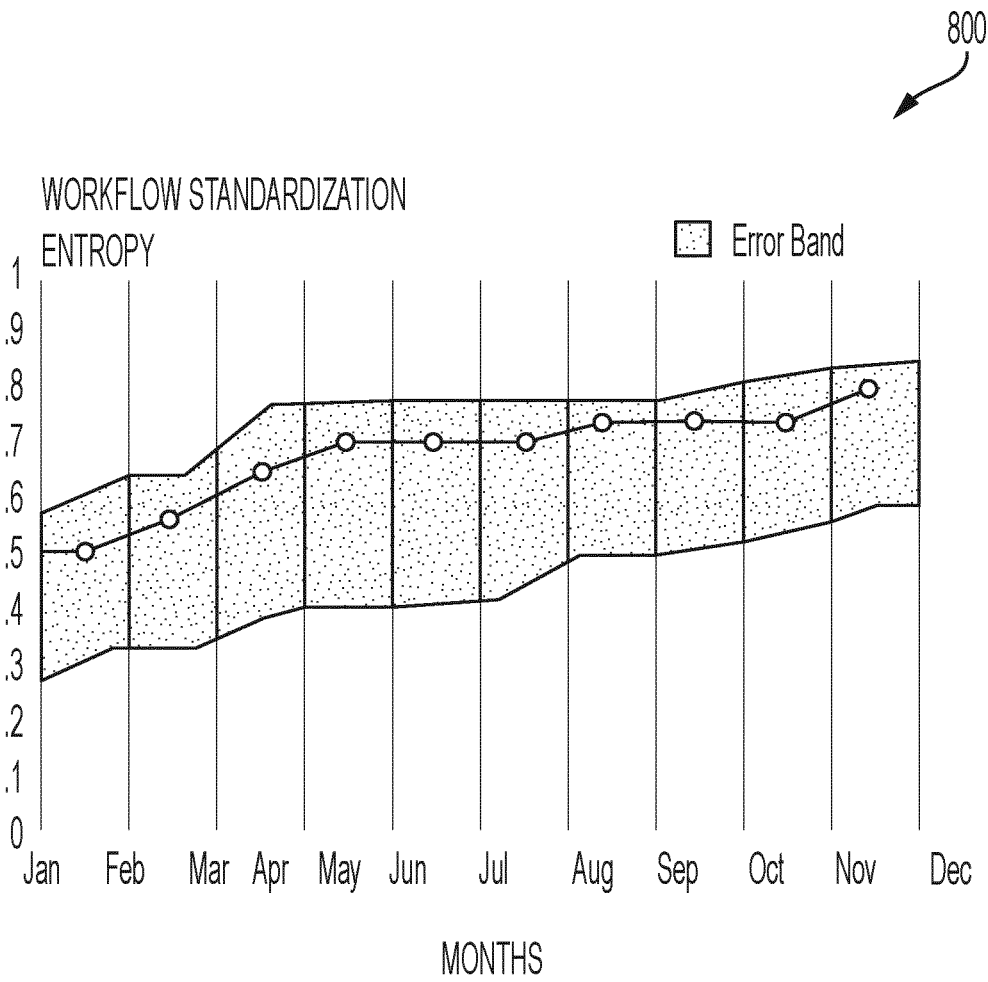
FIG. 8 depicts an example of a visualization of workflow standardization according to one or more aspects.

Turning now to FIG. 8, an example of a visualization 800 of workflow standardization is generally shown in accordance with one or more aspects. The visualization 800 shown in FIG. 8 shows the average entropy of a surgery each month with the shaded sections corresponding to the error bands of the calculation. This shows the potential error of the entropy calculation based on the number of surgeries carried out each month as described previously.

Figure 9:
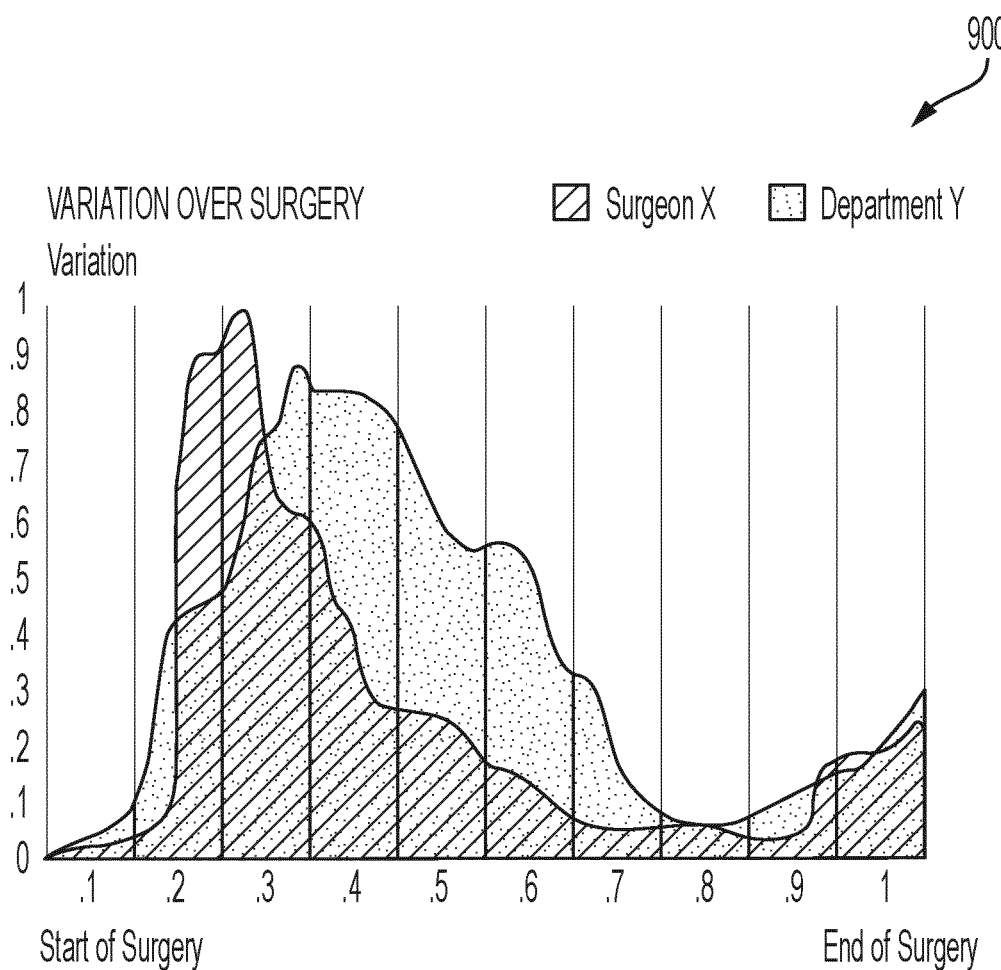
FIG. 9 depicts an example of a visualization of variation over surgery according to one or more aspects.

Turning now to FIG. 9, an example of a visualization 900 of variation over surgery is generally shown in accordance with one or more aspects. This shows the entropy throughout a surgery from the start point 0 on the left to the end of the surgery at Point 1 on the right. The entropy throughout the surgery is shown for a particular surgeon in blue compared to the relevant department in pink. This allows users to compare their variation with that of their department to determine whether their variation is in line with their peers.

Figure 10:
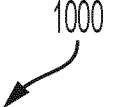
FIG. 10 depicts an example of a visualization of aligned sequences according to one or more aspects.
Figure 10:
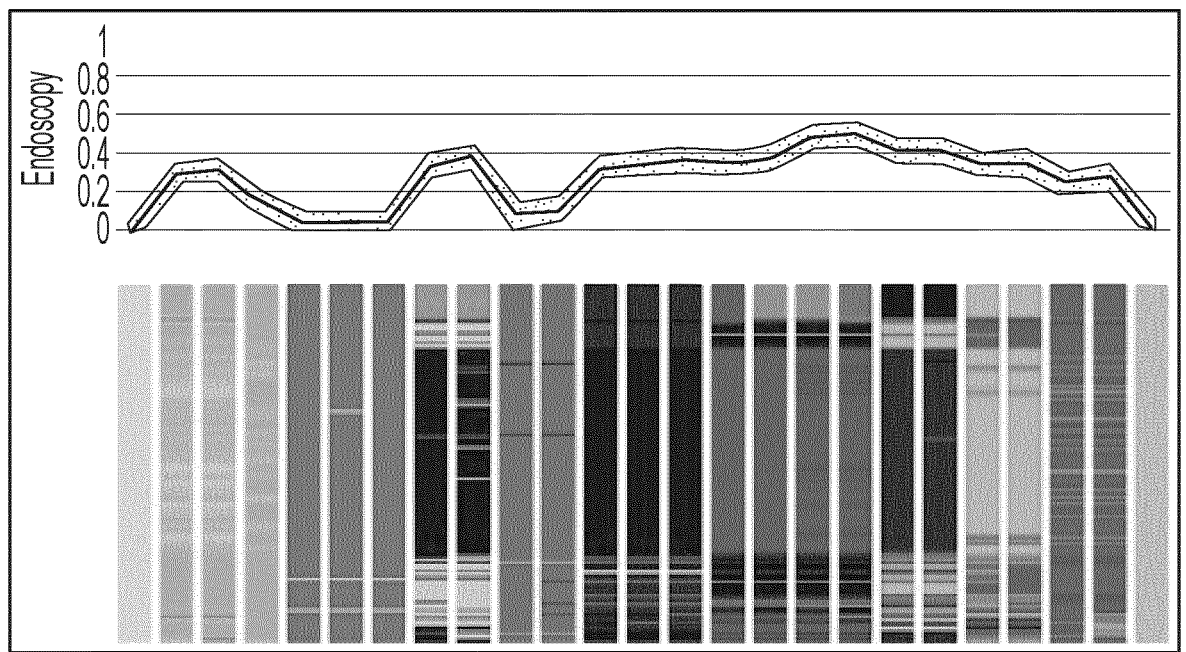

Turning now to FIG. 10, an example of a visualization 1000 of aligned sequences is generally shown in accordance with one or more aspects. As shown in the visualization of FIG. 10, a graph showing an entropy valued scaled between zero and one is shown for each of the elements in the aligned sequences. The blue shaded area corresponds to the error bands for the calculation. The colored bars below show the aligned sequences with each color representing a different phase in the surgery and one row corresponding to one recorded surgery. This can be used to show the amount of variation in the surgical procedure over time for the set of videos that were analyzed.

The visualizations 800 900 1000 shown in FIG. 8, FIG. 9, and FIG. 10, respectively, are examples of the type of data that may be generated and displayed to a user. In according to aspects, a graphical representation of the identified surgical approaches (or other data) is output for display on a display device. User input may be received via a user interface of the graphical representation and a second graphical representation including for example, providers that use one or more of the identified surgical approaches, may be output for display on the display device. In this manner, the visualization is interactive and can be modified based on input from a user. One skilled in the art will appreciate that any number of different visualizations containing different data and in different formats can be provided by the surgical variation visualization module 406 of FIG. 4 based on contents of the surgical workflow data for output to display device 410 of FIG. 4.

Figure 11:
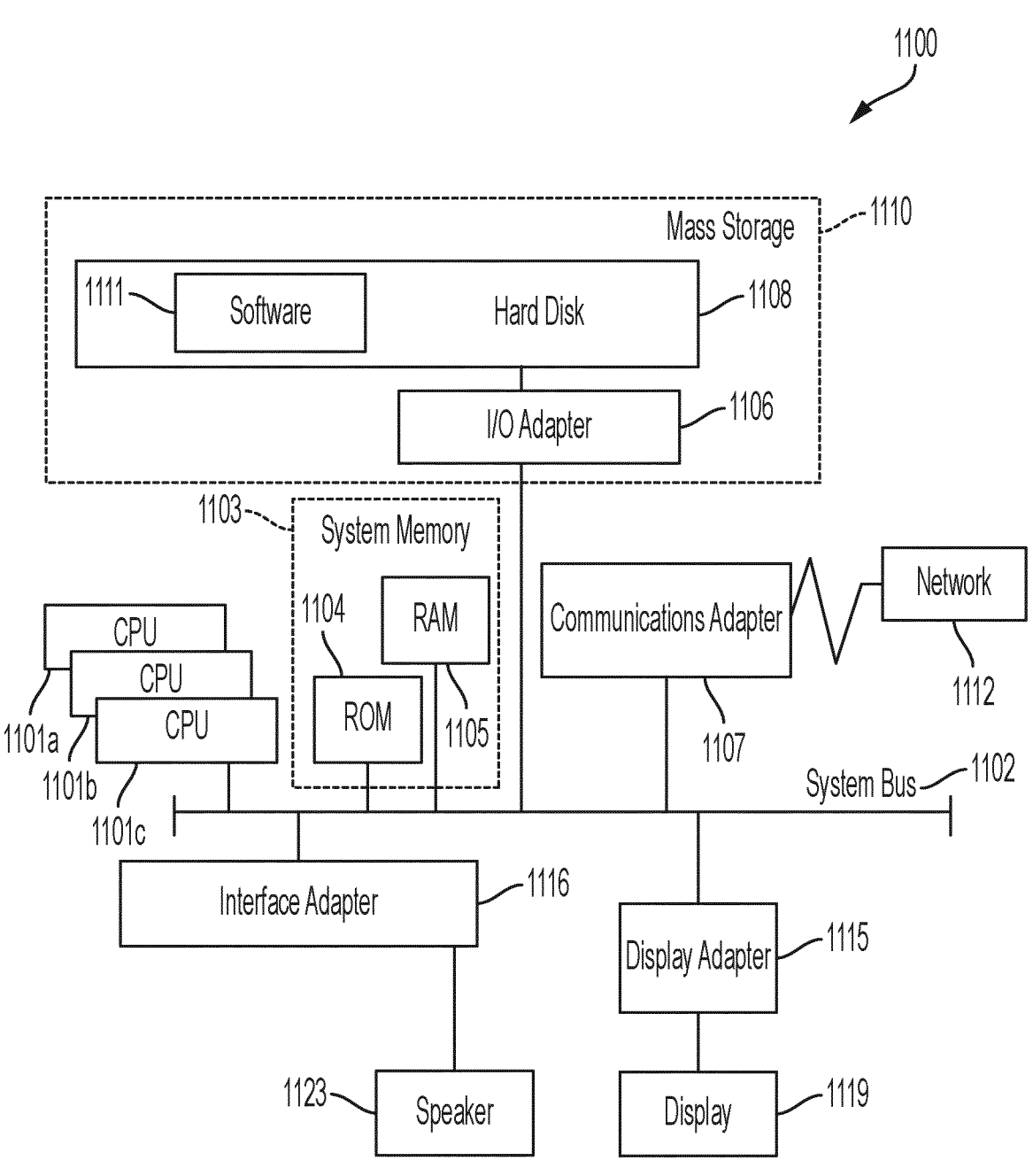
FIG. 11 depicts a computer system according to one or more aspects.

Turning now to FIG. 11, a computer system 1100 is generally shown in accordance with an aspect. The computer system 1100 can be an electronic computer framework comprising and/or employing any number and combination of computing devices and networks utilizing various communication technologies, as described herein. The computer system 1100 can be easily scalable, extensible, and modular, with the ability to change to different services or reconfigure some features independently of others. The computer system 1100 may be, for example, a server, desktop computer, laptop computer, tablet computer, or smartphone. In some examples, computer system 1100 may be a cloud computing node. Computer system 1100 may be described in the general context of computer-executable instructions, such as program modules, being executed by a computer system. Generally, program modules may include routines, programs, objects, components, logic, data structures, and so on that perform particular tasks or implement particular abstract data types. Computer system 1100 may be practiced in distributed cloud computing environments where tasks are performed by remote processing devices that are linked through a communications network. In a distributed cloud computing environment, program modules may be located in both local and remote computer system storage media, including memory storage devices.

As shown in FIG. 11, the computer system 1100 has one or more central processing units (CPU(s)) 1101*a*, 1101*b*, 1101*c*, etc. (collectively or generically referred to as processor(s) 1101). The processors 1101 can be a single-core processor, multi-core processor, computing cluster, or any number of other configurations. The processors 1101, also referred to as processing circuits, are coupled via a system bus 1102 to a system memory 1103 and various other components. The system memory 1103 can include one or more memory devices, such as read-only memory (ROM) 1104 and a random-access memory (RAM) 1105. The ROM 1104 is coupled to the system bus 1102 and may include a basic input/output system (BIOS), which controls certain basic functions of the computer system 1100. The RAM is read-write memory coupled to the system bus 1102 for use by the processors 1101. The system memory 1103 provides temporary memory space for operations of said instructions during operation. The system memory 1103 can include random access memory (RAM), read-only memory, flash memory, or any other suitable memory systems.

The computer system 1100 comprises an input/output (I/O) adapter 1106 and a communications adapter 1107 coupled to the system bus 1102. The I/O adapter 1106 may be a small computer system interface (SCSI) adapter that communicates with a hard disk 1108 and/or any other similar component. The I/O adapter 1106 and the hard disk 1108 are collectively referred to herein as a mass storage 1110.

Software 1111 for execution on the computer system 1100 may be stored in the mass storage 1110. The mass storage 1110 is an example of a tangible storage medium readable by the processors 1101, where the software 1111 is stored as instructions for execution by the processors 1101 to cause the computer system 1100 to operate, such as is described hereinbelow with respect to the various Figures. Examples of computer program product and the execution of such instruction is discussed herein in more detail. The communications adapter 1107 interconnects the system bus 1102 with a network 1112, which may be an outside network, enabling the computer system 1100 to communicate with other such systems. In one aspect, a portion of the system memory 1103 and the mass storage 1110 collectively store an operating system, which may be any appropriate operating system to coordinate the functions of the various components shown in FIG. 11.

Additional input/output devices are shown as connected to the system bus 1102 via a display adapter 1115 and an interface adapter 1116 and. In one aspect, the adapters 1106, 1107, 1115, and 1116 may be connected to one or more I/O buses that are connected to the system bus 1102 via an intermediate bus bridge (not shown). A display 1119 (e.g., a screen or a display monitor) is connected to the system bus 1102 by a display adapter 1115, which may include a graphics controller to improve the performance of graphics-intensive applications and a video controller. A keyboard, a mouse, a touchscreen, one or more buttons, a speaker, etc., can be interconnected to the system bus 1102 via the interface adapter 1116, which may include, for example, a Super I/O chip integrating multiple device adapters into a single integrated circuit. Suitable I/O buses for connecting peripheral devices such as hard disk controllers, network adapters, and graphics adapters typically include common protocols, such as the Peripheral Component Interconnect (PCI). Thus, as configured in FIG. 11, the computer system 1100 includes processing capability in the form of the processors 1101, and storage capability including the system memory 1103 and the mass storage 1110, input means such as the buttons, touchscreen, and output capability including the speaker 1123 and the display 1119.

In some aspects, the communications adapter 1107 can transmit data using any suitable interface or protocol, such as the internet small computer system interface, among others. The network 1112 may be a cellular network, a radio network, a wide area network (WAN), a local area network (LAN), or the Internet, among others. An external computing device may connect to the computer system 1100 through the network 1112. In some examples, an external computing device may be an external web server or a cloud computing node.

It is to be understood that the block diagram of FIG. 11 is not intended to indicate that the computer system 1100 is to include all of the components shown in FIG. 11. Rather, the computer system 1100 can include any appropriate fewer or additional components not illustrated in FIG. 11 (e.g., additional memory components, embedded controllers, modules, additional network interfaces, etc.). Further, the aspects described herein with respect to computer system 1100 may be implemented with any appropriate logic, wherein the logic, as referred to herein, can include any suitable hardware (e.g., a processor, an embedded controller, or an application-specific integrated circuit, among others), software (e.g., an application, among others), firmware, or any suitable combination of hardware, software, and firmware, in various aspects.

The present invention may be a system, a method, and/or a computer program product at any possible technical detail level of integration. The computer program product may include a computer-readable storage medium (or media) having computer-readable program instructions thereon for causing a processor to carry out aspects of the present invention.

The computer-readable storage medium can be a tangible device that can retain and store instructions for use by an instruction execution device. The computer-readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer-readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer-readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer-readable program instructions described herein can be downloaded to respective computing/processing devices from a computer-readable storage medium or to an external computer or external storage device via a network, for example, the Internet, a local area network, a wide area network, and/or a wireless network. The network may comprise copper transmission cables, optical transmission fibers, wireless transmission, routers, firewalls, switches, gateway computers, and/or edge servers. A network adapter card or network interface in each computing/processing device receives computer-readable program instructions from the network and forwards the computer-readable program instructions for storage in a computer-readable storage medium within the respective computing/processing device.

Computer-readable program instructions for carrying out operations of the present invention may be assembler instructions, instruction-set-architecture (ISA) instructions, machine instructions, machine-dependent instructions, microcode, firmware instructions, state-setting data, configuration data for integrated circuitry, or either source-code or object code written in any combination of one or more programming languages, including an object-oriented programming language such as Smalltalk, C++, or the like, and procedural programming languages, such as the "C" programming language or similar programming languages. The computer-readable program instructions may execute entirely on the user's computer, partly on the user's computer, as a stand-alone software package, partly on the user's computer and partly on a remote computer, or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some aspects, electronic circuitry including, for example, programmable logic circuitry, field-programmable gate arrays (FPGA), or programmable logic arrays (PLA) may execute the computer-readable program instruction by utilizing state information of the computer-readable program instructions to personalize the electronic circuitry, in order to perform aspects of the present invention.

Aspects of the present invention are described herein with reference to flowchart illustrations and/or block diagrams of methods, apparatus (systems), and computer program products according to aspects of the invention. It will be understood that each block of the flowchart illustrations and/or block diagrams, and combinations of blocks in the flowchart illustrations and/or block diagrams, can be implemented by computer-readable program instructions.

These computer-readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer-readable program instructions may also be stored in a computer-readable storage medium that can direct a computer, a programmable data processing apparatus, and/or other devices to function in a particular manner, such that the computer-readable storage medium having instructions stored therein comprises an article of manufacture including instructions which implement aspects of the function/act specified in the flowchart and/or block diagram block or blocks.

The computer-readable program instructions may also be loaded onto a computer, other programmable data processing apparatus, or other device to cause a series of operational steps to be performed on the computer, other programmable apparatus or other devices to produce a computer-implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various aspects of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various aspects of the present invention have been presented for purposes of illustration but are not intended to be exhaustive or limited to the aspects disclosed. Many modifications and variations will be apparent to those of ordinary skill in the art without departing from the scope and spirit of the described aspects. The terminology used herein was chosen to best explain the principles of the aspects, the practical application or technical improvement over technologies found in the marketplace, or to enable others of ordinary skill in the art to understand the aspects described herein.

Various aspects of the invention are described herein with reference to the related drawings. Alternative aspects of the invention can be devised without departing from the scope of this invention. Various connections and positional relationships (e.g., over, below, adjacent, etc.) are set forth between elements in the following description and in the drawings. These connections and/or positional relationships, unless specified otherwise, can be direct or indirect, and the present invention is not intended to be limiting in this respect. Accordingly, a coupling of entities can refer to either a direct or an indirect coupling, and a positional relationship between entities can be a direct or indirect positional relationship. Moreover, the various tasks and process steps described herein can be incorporated into a more comprehensive procedure or process having additional steps or functionality not described in detail herein.

The following definitions and abbreviations are to be used for the interpretation of the claims and the specification. As used herein, the terms "comprises," "comprising," "includes," "including," "has," "having," "contains," or "containing," or any other variation thereof are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any aspect or design described herein as "exemplary" is not necessarily to be construed as preferred or advantageous over other aspects or designs. The terms "at least one" and "one or more" may be understood to include any integer number greater than or equal to one, i.e., one, two, three, four, etc. The terms "a plurality" may be understood to include any integer number greater than or equal to two, i.e., two, three, four, five, etc. The term "connection" may include both an indirect "connection" and a direct "connection."

The terms "about," "substantially," "approximately," and variations thereof are intended to include the degree of error associated with measurement of the particular quantity based upon the equipment available at the time of filing the application. For example, "about" can include a range of ±8% or 5%, or 2% of a given value.

For the sake of brevity, conventional techniques related to making and using aspects of the invention may or may not be described in detail herein. In particular, various aspects of computing systems and specific computer programs to implement the various technical features described herein are well known. Accordingly, in the interest of brevity, many conventional implementation details are only mentioned briefly herein or are omitted entirely without providing the well-known system and/or process details.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general-purpose microprocessors, application-specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A system comprising:
a machine learning training system comprising one or more machine learning models that are trained to identify a plurality of surgical phases in a video of a surgical procedure; and
a data analysis system configured to quantify variation in surgical approaches in a plurality of videos capturing a same type of surgical procedure, wherein the quantifying variation in surgical approaches comprises:
    receiving a plurality of surgical videos, each of the plurality of surgical videos capturing a workflow of the same type of surgical procedure;
    segmenting each of the plurality of surgical videos into a segmented workflow comprising a plurality of surgical phases, the segmenting based on surgical phases identified by the machine learning training system;
    aligning phases in the segmented workflows to an average workflow of the segmented workflows to create a plurality of aligned workflows, wherein the average workflow is calculated based on the workflows captured in the plurality of surgical videos by analyzing a plurality of medoid workflows in the plurality of surgical videos, selecting the average workflow from the plurality of medoid workflows, and executing adaptive dynamic time warping-bary-center-averaging (ADBA) using each of the medoid workflows as an initial average, and wherein the analyzing is optimized for categoric data and is based at least in part on mode values of phases across the segmented workflows;
    calculating an entropy for each phase in the aligned workflows, the calculating based on a Chao-Shen estimator which reduces bias for small sample sizes; and
    outputting the entropy for each phase in the aligned workflows to a display device for display, wherein the entropy represents variation in surgical approaches to the surgical procedure.

2. The system of claim 1, wherein calculating the entropy comprises scaling the entropy by its maximum possible value to a value that falls in a specified range of values.

3. The system of claim 1, wherein the optimization comprises modifying a length of the average workflow by one of adding a phase to the average workflow or removing a phase from the average workflow.

4. The system of claim 1, wherein the outputting further comprises outputting an indication of a surgical service provider associated with one or more of the aligned workflows to the display device for display.

5. A computer-implemented method comprising:
receiving, by a processor, a plurality of surgical videos, each of the plurality of surgical videos capturing a workflow of a same type of surgical procedure and each of the plurality of surgical videos segmented into a segmented workflow comprising surgical phases;
analyzing a plurality of the segmented workflows to calculate an average workflow, wherein the average workflow is calculated based on the workflows captured in the plurality of surgical videos by analyzing a plurality of medoid workflows in the plurality of surgical videos, selecting the average workflow from the plurality of medoid workflows, and executing adaptive dynamic time warping-barycenter-averaging (ADBA) using each of the medoid workflows as an initial average, and wherein the analyzing is optimized for categoric data and is based at least in part on mode values of phases across the segmented workflows;

aligning the plurality of the segmented workflows to the average workflow; and based on the aligning, quantifying a variation in the surgical approaches in the plurality of segmented workflows.

6. The computer-implemented method of claim 5, wherein the analyzing is optimized for categoric data and is based at least in part on mode values of phases across the segmented workflows.

7. The computer-implemented method of claim 6, wherein the optimization comprises modifying a length of the average workflow by one of adding a phase to the average workflow or removing a phase from the average workflows.

8. The computer-implemented method of claim 5, further comprising outputting, by the processor to a display device, a graphical representation of the aligned segmented workflows and the variation in the surgical approaches.

9. The computer-implemented method of claim 8, wherein the graphical representation identifies a surgical service provider associated with each of the workflows.

10. The computer-implemented method of claim 5, wherein a scaled entropy value is used to quantify the variation in the surgical approaches.

11. A computer program product comprising a memory device having computer-executable instructions stored thereon, which when executed by one or more processors cause the one or more processors to perform operations comprising:

visualizing variations in surgical approaches to performing a surgical procedure, the visualizing comprising:

receiving a plurality of surgical videos, each of the plurality of surgical videos capturing a workflow of a same type of surgical procedure and each of the plurality of surgical videos segmented into a segmented workflow comprising surgical phases;

analyzing a plurality of the segmented workflows to calculate an average workflow, wherein the average workflow is calculated based on the workflows captured in the plurality of surgical videos by analyzing a plurality of medoid workflows in the plurality of surgical videos, selecting the average workflow from the plurality of medoid workflows, and executing adaptive dynamic time warping-barycenter-averaging (ADBA) using each of the medoid workflows as an initial average, and wherein the analyzing is optimized for categoric data and is based at least in part on mode values of phases across the segmented workflows;

aligning the plurality of the segmented workflows to the average workflow;

based on the aligning, quantifying a variation in the workflows in the plurality of surgical videos; and outputting to a display device, a graphical representation of the quantified variation.

12. The computer program product of claim 11, wherein the visualizing further comprises:

receiving user input via a user interface of the graphical representation; and in response to the user input, outputting to the display device, a second graphical representation that includes additional information describing characteristics of one or both of a service provider or a patient.

13. The computer program product of claim 11, wherein the graphical representation of the quantified variation comprises a graph of the variation over a duration of the surgical procedure.

14. The computer program product of claim 11, wherein each of the plurality of surgical videos is segmented into surgical phases, and the quantifying is based at least in part on the surgical phases.

\* \* \* \* \*